United States Patent
Durkin

(10) Patent No.: US 8,633,454 B2
(45) Date of Patent: Jan. 21, 2014

(54) STERILISING APPARATUS

(75) Inventor: Anne Marie Durkin, Lismacaffrey (IE)

(73) Assignee: Shasta Limited, Granard (IE)

( * ) Notice: Subject to any disclaimer, the term of this patent is extended or adjusted under 35 U.S.C. 154(b) by 241 days.

(21) Appl. No.: 13/321,969

(22) PCT Filed: May 24, 2010

(86) PCT No.: PCT/EP2010/057092
§ 371 (c)(1),
(2), (4) Date: Nov. 22, 2011

(87) PCT Pub. No.: WO2010/133698
PCT Pub. Date: Nov. 25, 2010

(65) Prior Publication Data
US 2012/0068088 A1 Mar. 22, 2012

(30) Foreign Application Priority Data
May 22, 2009 (IE) .................................. S2009/0400

(51) Int. Cl.
*A61J 9/00* (2006.01)
*A61L 2/10* (2006.01)
*G01N 23/00* (2006.01)
*H01J 37/20* (2006.01)

(52) U.S. Cl.
USPC ............... 250/455.11; 250/461.1; 250/504 H; 250/504 R; 215/11.6; 248/102; 422/24

(58) Field of Classification Search
USPC ............... 250/453.11, 454.11, 455.11, 461.1, 250/492.1, 504 R, 504 H, 526; 141/29, 147, 141/276; 422/24; 215/11.1, 11.6, 386, 393, 215/400; 245/102, 694; 248/102, 694
See application file for complete search history.

(56) References Cited

U.S. PATENT DOCUMENTS

| | | | | |
|---|---|---|---|---|
| 2,347,150 A | * | 4/1944 | Consolazio | 220/265 |
| 3,248,231 A | * | 4/1966 | Wilson et al. | 426/87 |
| 3,301,423 A | * | 1/1967 | Soto | 215/11.6 |
| 4,840,424 A | * | 6/1989 | Asoh | 296/204 |
| 6,171,623 B1 | * | 1/2001 | Gaylor et al. | 426/117 |
| 7,100,782 B2 | * | 9/2006 | Hanna | 215/11.6 |
| 7,703,262 B2 | * | 4/2010 | Till | 53/426 |
| 8,399,853 B2 | * | 3/2013 | Roiniotis | 250/455.11 |
| 2002/0146343 A1 | * | 10/2002 | Jenkins et al. | 422/24 |
| 2004/0074859 A1 | * | 4/2004 | Hanna | 215/11.1 |
| 2004/0123885 A1 | * | 7/2004 | Myong | 134/168 R |
| 2006/0011263 A1 | | 1/2006 | Till | |
| 2006/0147339 A1 | * | 7/2006 | Hunter et al. | 422/24 |

(Continued)

FOREIGN PATENT DOCUMENTS

EP 1120121 1/2001
EP 1614630 1/2006

(Continued)

*Primary Examiner* — Bernard E Souw
(74) *Attorney, Agent, or Firm* — The Webb Law Firm

(57) ABSTRACT

A sterilizing apparatus for sterilizing a feeding bottle assembly for a baby, the feeding bottle assembly comprising a feeding bottle, a top end and a base end, the top end having an open neck; the sterilizing apparatus comprising a housing which is adapted to attach to and sit on the top end of the bottle, an ultraviolet (UV) light source on the housing which extends into the bottle for UV sterilization of the bottle when the housing is attached to the bottle, and a switch which automatically switches on the UV light source when the sterilizing apparatus is attached to the bottle.

20 Claims, 29 Drawing Sheets

(56) References Cited

U.S. PATENT DOCUMENTS

| | | |
|---|---|---|
| 2007/0164232 A1 | 7/2007 | Rolleri et al. |
| 2009/0166310 A1* | 7/2009 | Cote et al. .................... 215/11.6 |
| 2010/0112180 A1* | 5/2010 | Laniado ........................ 426/590 |
| 2010/0143188 A1* | 6/2010 | Roiniotis ........................ 422/24 |

FOREIGN PATENT DOCUMENTS

| | | |
|---|---|---|
| JP | 2002191678 | 7/2002 |
| WO | 9908933 | 2/1999 |
| WO | 0038740 | 7/2000 |
| WO | 2004031706 | 4/2004 |

\* cited by examiner

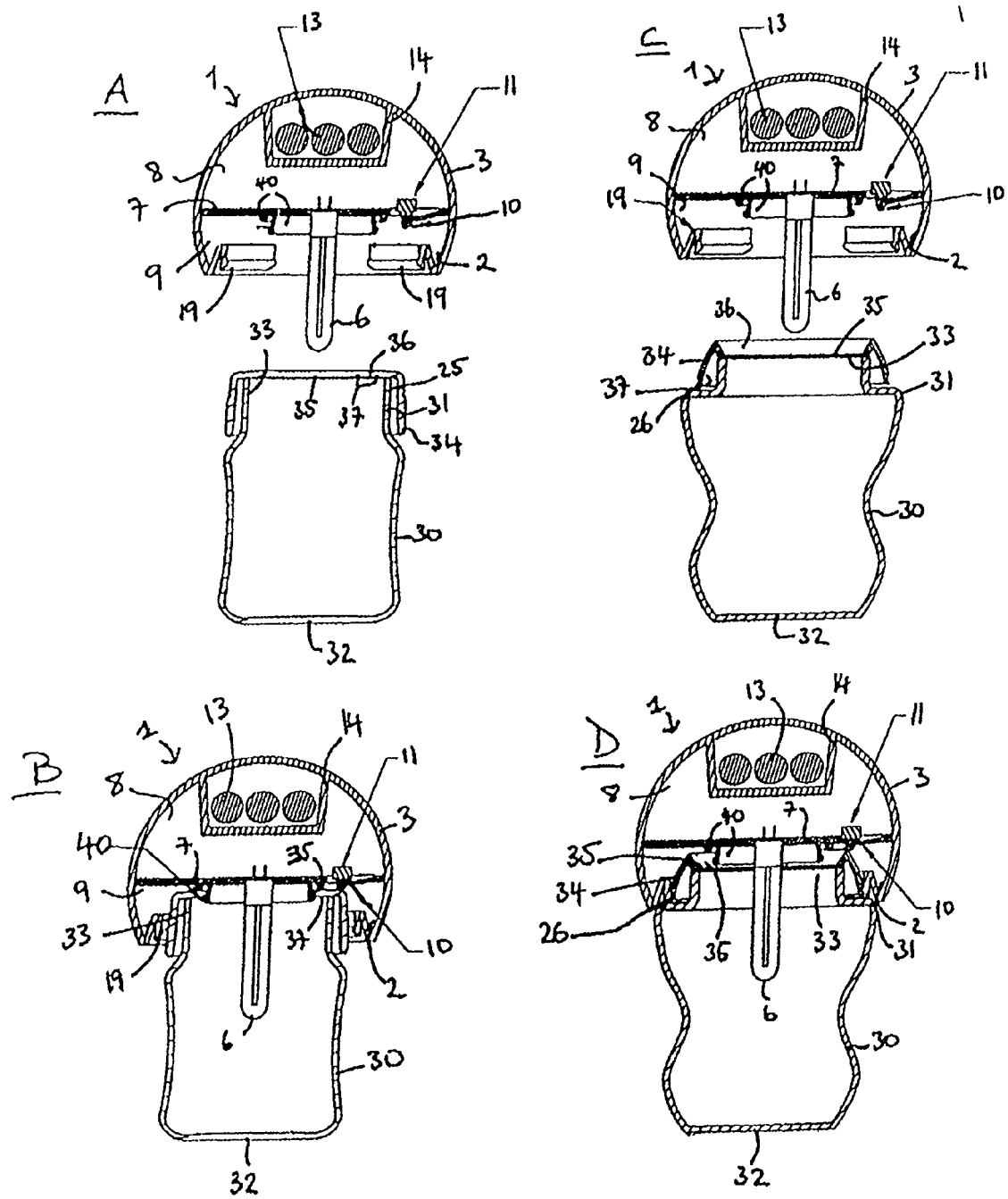

Fig. 10
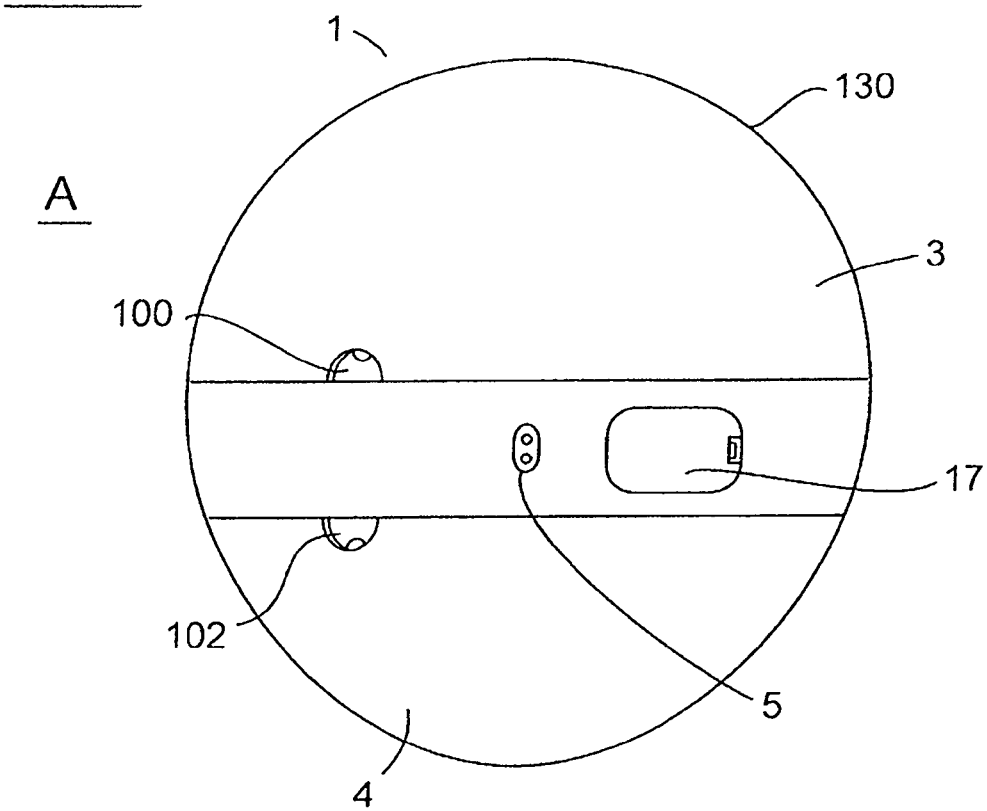
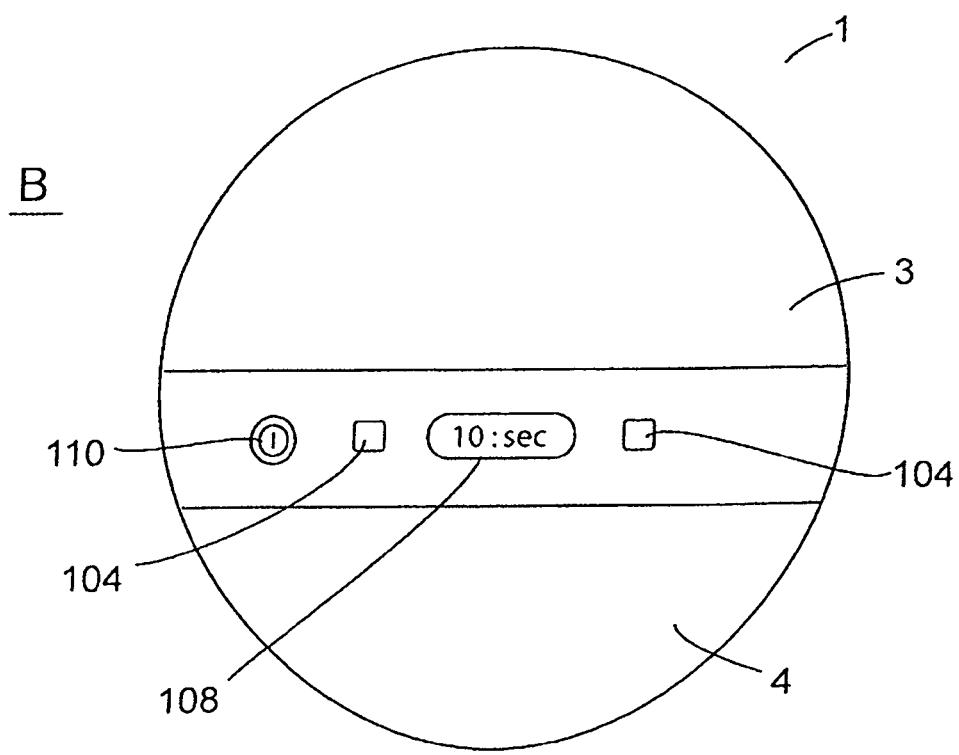

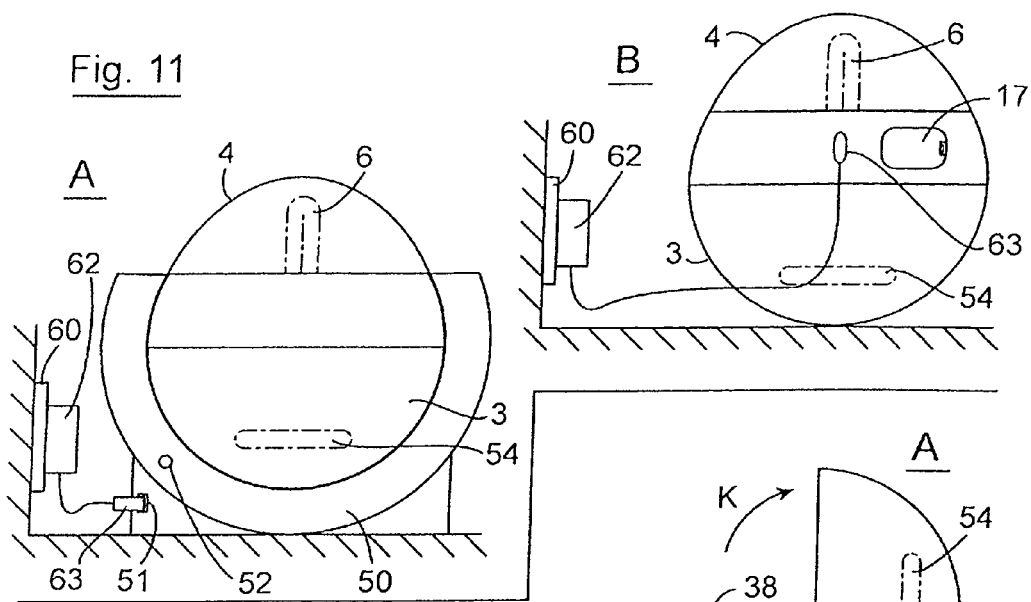
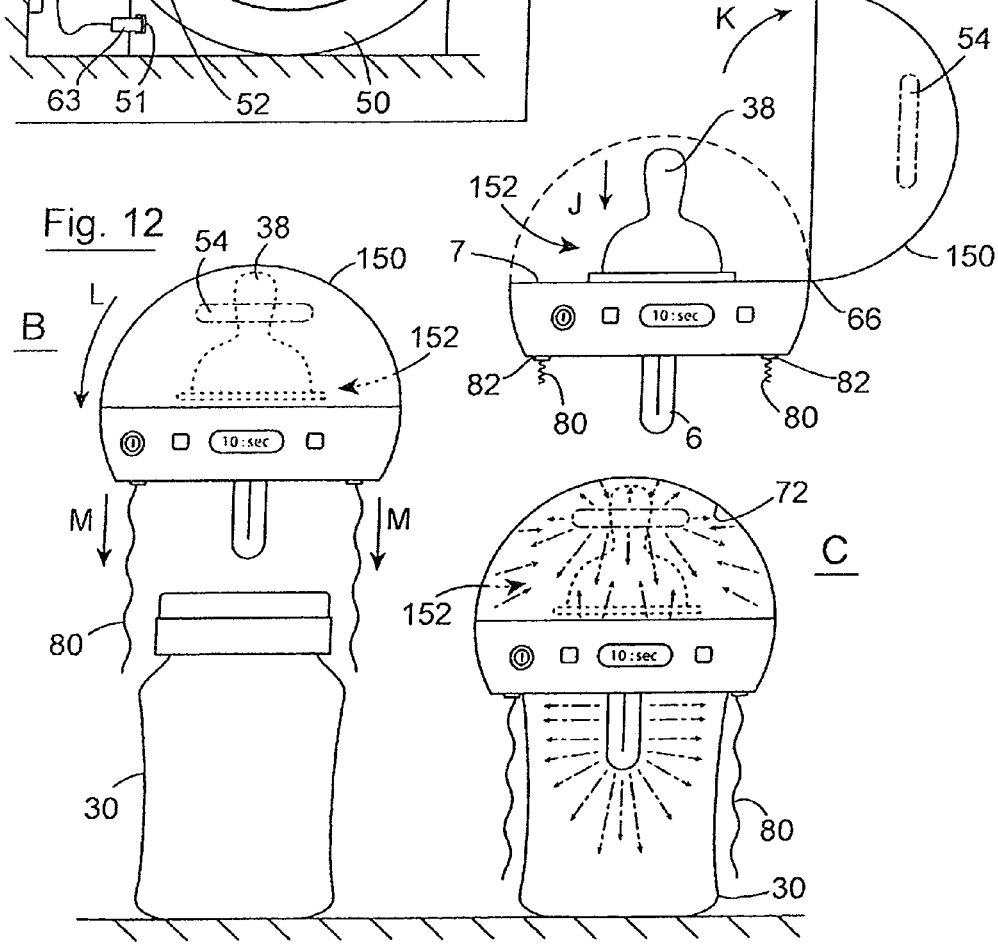

Fig. 14
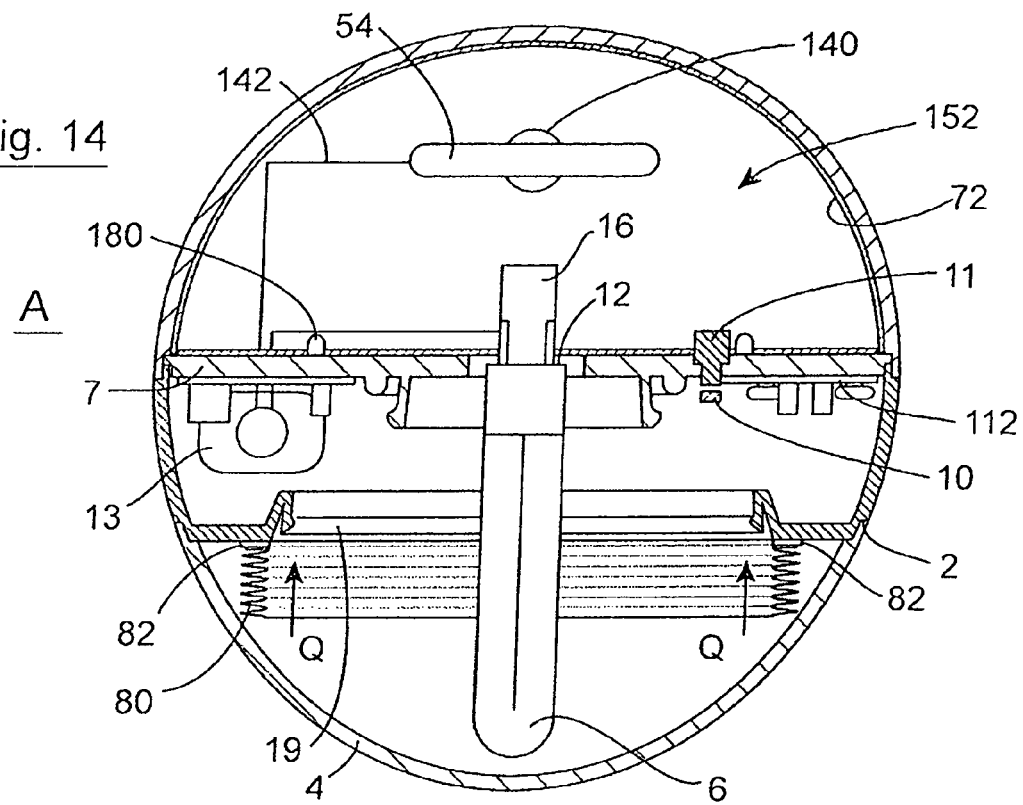
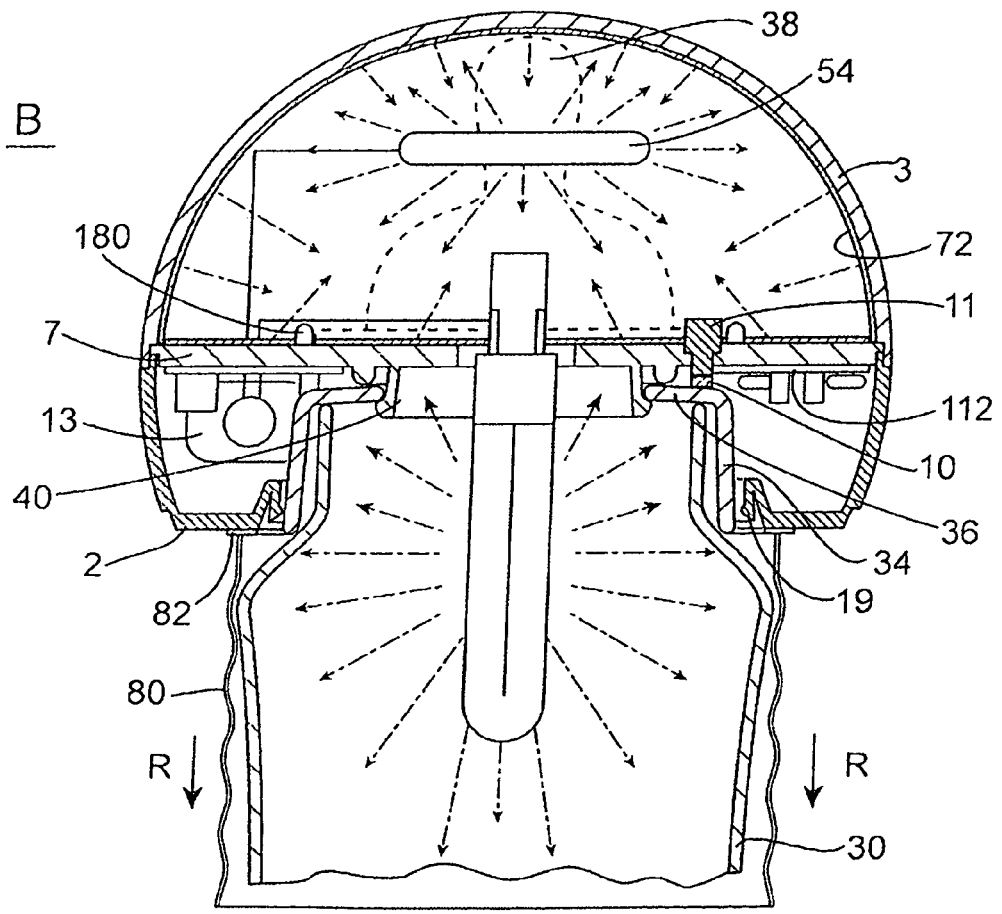

Fig. 15
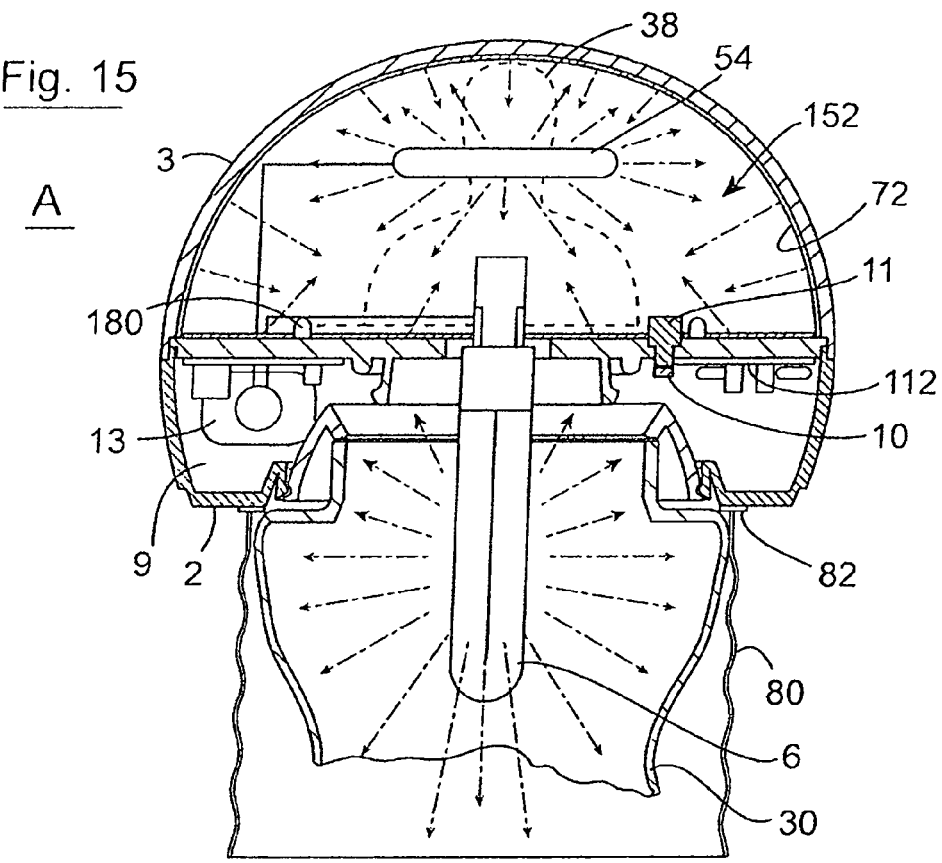
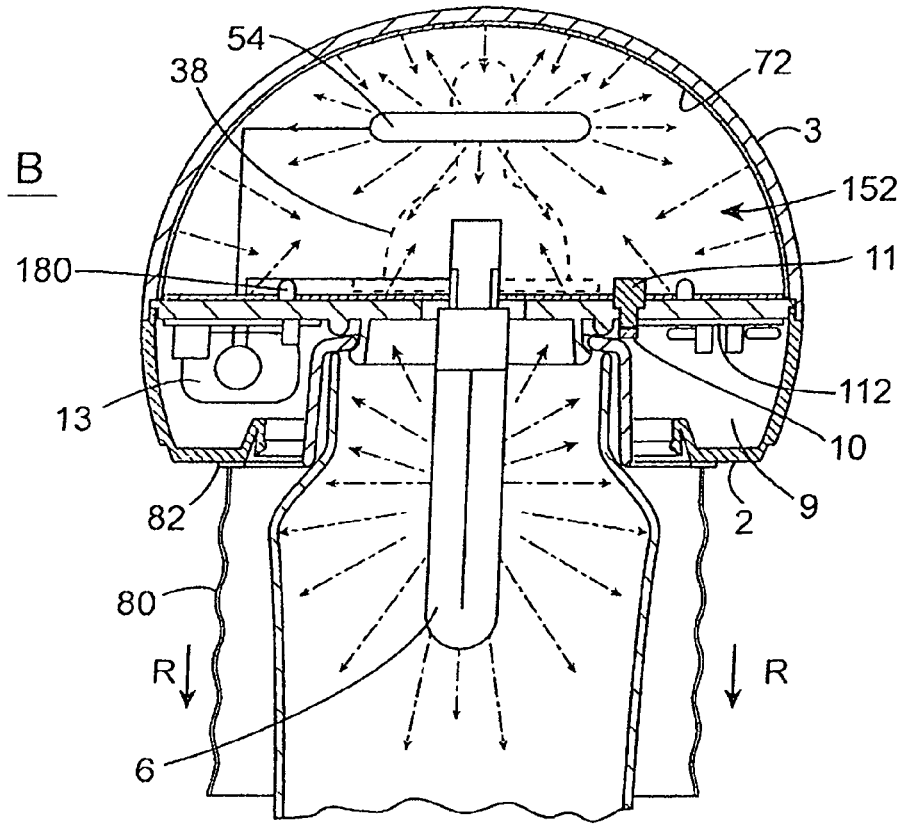

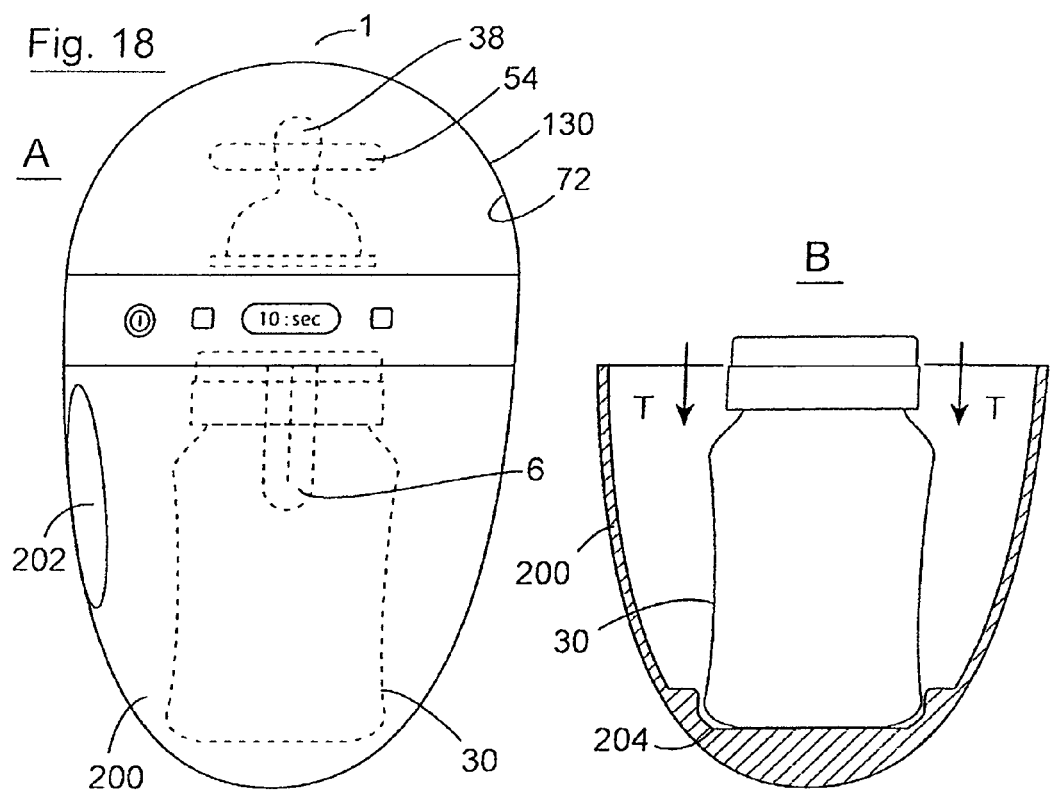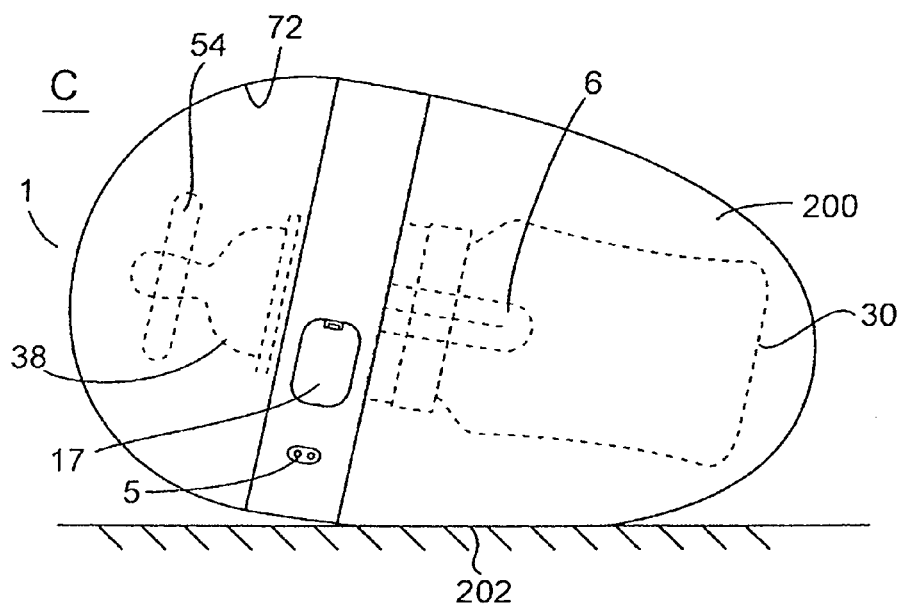

Fig. 19
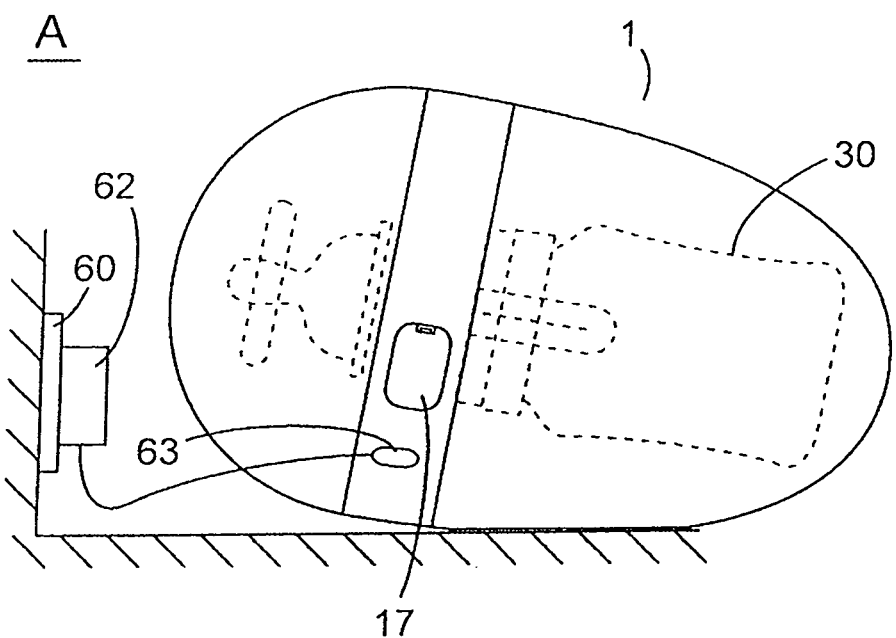
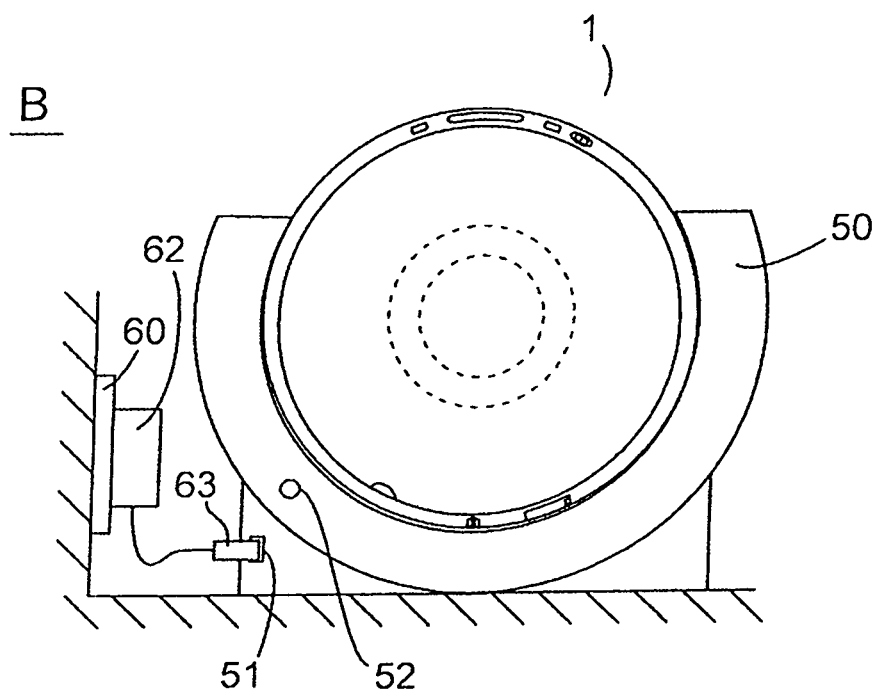

E.coli

*E. hirae*

*S. aureus*

Replicate *S. aureus*

*S. mutans*

*Pseudomonas aeroginosa*

*Staphyloccocus aureus*

Log count (*S. aureus* colony) versus time – 100% kill ≤ 20s

Log count (*E. hirae* colony) versus time – 100% kill ≤ 40s

Log count (*E. coli* colony) versus time – 100% kill ≤ 17s

Log count (milk residue colonies) versus time – 100% kill ≤ 50.

STERILISING APPARATUS

FIELD OF THE INVENTION

The present invention relates to apparatus and methods for sterilising containers, and in particular, for sterilising baby feeding bottles.

BACKGROUND TO THE INVENTION

There are a wide range of sterilising devices known for sterilising baby/infant equipment such as bottles, teats, soothers (pacifiers) and the like. As harmful bacteria grow quickly in milk, sterilising baby/infant feeding equipment is strongly recommended by general practitioners (GPs) and in particular to protect babies under 12 months of age against germs and infection as this group does not have a fully developed immune system. The most common form of sterilising units are those utilising water to create a sterilising solution in which the items are immersed, and steam units including those heated by electrical, and microwave energies.

The cold water type, generally, uses a large plastic container filled with either cold water into which is added chemicals for example sanitising tablets to form a sterilising/sanitising solution, or a commercially available chemical sterilising solution. The underlying problems with this method are that the objects to be sterilised are required to be immersed in the sterilising solution for prolonged periods of time, generally up to and over an hour, before they are considered to be sufficiently sterilised, for example, feeding bottles for babies/infants. The sterilised items must then be rinsed in recently boiled water before use. Furthermore, due to the buoyant nature of some equipment such as bottles and bottle teats, these tend to float on the surface of the solution. As such, those items may not be fully sterilised and pose a risk to the infant. As chemicals are used in the sterilising solution method, the general public are less inclined to utilise the sterilising solution method, and thus the use of this method is becoming less popular.

One type of electrical sterilisers utilise steam and require no chemicals or rinsing, and simply plug into a mains socket in a wall. The heat of the steam is sufficient to kill bacteria and sterilisation usually takes 8-15 minutes depending on the commercial unit. Generally a hotplate or some other electrical heating element that is powered by electricity generates sufficient heat to generate steam from added water. Microwave sterilisers also do not require chemicals or rinsing, and kill bacteria using steam heat generated by microwave irradiation of water. Generally such units are designed to be placed in a conventional household microwave so do not have an integral microwave source. Sterilisation takes at least 3 minutes, for example from 5 to 10 minutes in a microwave (depending on the microwave wattage). In both cases items generally remain sterile for up to 3 hours if kept within the sterilising unit. Electrical sterilisers are convenient if a microwave is not available and/or a lot of items require sterilisation. However, the problems in using steam to sterilise baby/infant items is that if the sterilising unit is opened prematurely, the hot steam may cause burns to the user. Furthermore, a source of electricity is necessary to provide the energy required to boil water and produce steam, which may be problematic when a parent is travelling with an infant. In addition, the bulkiness of sterilisers make them an inconvenient means of sterilising baby feeding bottles, for example, when a parent is travelling with a baby/infant.

Microwave sterilisers can also double as cold water sterilisers if a source of electricity or microwave is unavailable. However, the problems associated with chemical sterilisation are outlined above.

The use of (ultraviolet) UV light to sterilise work surfaces, equipment and the like require an external source of power, such as a wall socket, to produce a continuous stream of UV light. International Patent Publication No. WO 99/08933 describes a system for sterilising bottles utilising UV light to generate ozone that is in turn used for sterilisation. International Patent Publication No. WO 00/38740 attempted to address the issue of non-portability of sterilising equipment by providing a chamber in which small objects such as bottle nipples (teats), pacifiers, teething rings, etc. can be placed for sterilisation by pulses of UV radiation. The device has a lockout function that prevents operation of the steriliser unless the object to be sterilised is in the chamber. Neither device is suitable for use for sterilising baby bottles.

A company trading under the trade name iLAB America Inc. sells a product under the brand name BBS-1, which is a portable baby bottle steriliser. The BBS-1 is a large cordless device comprising a chamber, a chamber door, and a UV light source within the chamber. A bottle to be sterilised is placed in the chamber and the chamber door must be completely closed in order for the UV light to operate. The BBS-1 is powered by rechargeable batteries or from a power source. The UV light source floods the chamber with UV light for three seconds to sterilise the bottle. The device is about twice the length of a large baby bottle and is thus bulky and heavy.

The problem with the above UV sterilisers is that they are either not suitable for use for sterilising baby bottles and/or are bulky and not convenient to carry around by a user.

SUMMARY OF THE INVENTION

In a first aspect the present invention provides a sterilising apparatus for sterilising a feeding bottle assembly for a baby, the feeding bottle assembly comprising:
  a feeding bottle, a top end and a base end, the top end having an open neck;
the sterilising apparatus comprising:
  a housing which is adapted to attach to and sit on the top end of the bottle,
  an ultraviolet (UV) light source on the housing which extends into the bottle for UV sterilisation of the bottle when the housing is attached to the bottle, and
  a switch which automatically switches on the UV light source when the sterilising apparatus is attached to the bottle.

One of the main advantages of the present invention is that the device is relatively small as compared to other sterilisers. As it fixes to the top end of the bottle assembly the bottle can wholly support the device when the bottle is standing on its base. It sits atop the bottle.

One advantage of the device of the invention is that it does not need to extend beyond the neck of the container. This allows for a very compact form of the device of the invention. The invention is portable and convenient when travelling. There is no need to have access to electricity (in general) or microwave, no sanitising tablets, chemicals or need for water/rinsing.

The disclosed present invention, which involves the use of ultra violet (UV) light sterilisation technology in a portable fashion, exceeds the convenience and requirements of the marketed sterilisation units, which use cold water, electrical and/or microwave means to sterilise baby feeding equipment and the like. In principle, the use of UV technology to sterilise baby/infant feeding equipment may be viewed as a more efficient and convenient means of killing bacteria and other harmful agents, which may be found on the surfaces of baby/infant feeding equipment. The disclosed invention has the potential to operate with a host of different shapes and sizes of branded baby feeding equipment, thereby providing an alternative, portable, and universal means of sterilising baby feeding equipment. If desired one or more adapters can be provided for attaching the device of the invention to bottles with differently sized open ends.

Sterilisation takes place automatically when the device of the invention is attached to the bottle. Desirably the switch is within the housing. This will mean there is no requirement for a manual switch that can be inadvertently activated, for example by accidental pressure whilst being carried.

In a second aspect of the present invention there is provided a sterilising apparatus for sterilising a feeding bottle assembly for a baby,
the feeding bottle assembly comprising:
a feeding bottle, a top end and a base end, the top end having an open neck;
the sterilising apparatus comprising:
a housing which is adapted to attach to and sit on the top end of the bottle,
an ultraviolet (UV) light source on the housing which extends into the bottle for UV sterilisation of the bottle when the housing is attached to the bottle, and
the sterilising apparatus being arranged to be self-righting.

In a third aspect the present invention provides a sterilising apparatus for sterilising a feeding bottle assembly for a baby,
the feeding bottle assembly comprising:
a feeding bottle, a top end and a base end, the top end having an open neck;
the sterilising apparatus comprising
a housing which is adapted to attach to and sit on the top end of the bottle, an ultraviolet (UV) light source on the housing which extends into the bottle for UV sterilisation of the bottle when the housing is attached to the bottle, the apparatus being arranged to sit on top of and be supported by the bottle.

In a fourth aspect the present invention provides a sterilising apparatus for sterilising a feeding bottle assembly for a baby,
the feeding bottle assembly comprising:
a feeding bottle, a top end and a base end, the top end having an open neck and a teat for the feeding bottle;
the sterilising apparatus comprising
a housing which is adapted to fit to the top end of the bottle,
an ultraviolet (UV) light source on the housing which extends into the bottle for UV sterilisation of the bottle when the housing is attached to the bottle, and
an enclosed chamber into which the teat may be placed for UV sterilisation.

It will be appreciated that any one or all aspects/features of the present invention outlined above may be combined in a single embodiment optionally with any one or all of the embodiments below.

The self-righting aspect of the invention is of interest as it means that the device of the invention will return to a desirable position even if placed in an undesirable position. For example it is desirable that the housing part of the device is protected from contamination. This can be achieved by ensuring that the housing is held away from any surface on which the device may be placed. Accordingly the self-righting arrangement may act so that in the righted position the housing is held upwards away from the surface. This can be achieved by suitable shaping and weight distribution that will ensure the device of the invention rolls toward the desired orientation even if it is left down in a different orientation. The device of the invention will thus not roll away, it will always sit upright.

The devices of the invention are truly portable and may be carried in a relatively small space. For example their entire volume may be comparable to that of a single bottle. The devices of the invention are easily hand-held and are easily fitted to a bottle. They are easy to fit in a small bag such as a handbag and are of a convenient size.

The devices of the present invention may also further comprise an enclosed chamber into which a teat for the bottle may be placed for UV sterilisation. The chamber may further comprise a UV light source for UV sterilisation of the teat. The chamber may be provided with one or more reflective surfaces. Any material which reflects UV light is suitable. For example, it may be coated with a reflective material. The purpose of the reflective surface(s) is to increase the exposure of the object to be sterilised to the UV light and ensure that the entire surface area of the teat is sterilised. It is desirable to sterilise a teat separately from the bottle to ensure that both are sterilised sufficiently and thoroughly for use.

The feeding bottle assembly may be more than just the bottle itself. It may further comprise a teat-retaining ring for sealing/engaging a teat to the open neck of the bottle fitted to the bottle. In such a case it is desirable that the housing attaches to the teat-retaining ring, for example to an exterior thereof. It may additionally or alternatively attach to an inner surface of the ring. In this way at least part of the interior of the ring may be sterilised also. It is desirable to sterilise at least part of the interior, for example an inner side such as an underside of the ring. In most bottles the ring may not come into contact with liquid (such as milk) in the bottle (it may be isolated from the liquid by a teat), but as the ring contacts the teat it is desirable to sterilise that part of the ring that may contact the teat.

A sterilising apparatus according to the present invention may further comprise an electronic control that automatically switches off the UV light source when a sterilising cycle has been completed. This means there is no requirement for the user to time a sterilising cycle. The entire sterilisation process may be automated to begin when the device of the invention is attached to the bottle assembly and finish when sufficient irradiation has taken place. The UV light source is desirably deactivated upon detaching the housing from the bottle assembly. This means that should the device of the invention be removed from a bottle assembly during sterilisation then the irradiation process is stopped automatically. Potentially harmful UV is not then emitted except when the device is attached to a bottle assembly.

In one desired aspect of the present invention, the predetermined sterilisation protocol comprises exposing the inner surface of the container to a cycle of UV radiation for between about 1 minute and about 20 minutes, preferably between about 2 minutes and about 15 minutes, more preferably between about 4 minutes and about 12 minutes, and even more preferably between about 8 minutes and about 10 minutes. With the invention it is possible to achieve sufficient sterilisation in less than 1 minute, for example less than 50 seconds, such as less than 40 seconds, including less than 30 seconds and indeed less than 20 seconds. In one arrangement sufficient sterilisation is achieved in less than 15 seconds for example within about 10 seconds.

The present inventor has found that when the bottle is made from polycarbonate an insignificant amount of UV escapes through the bottle. For the purposes of the present invention bottles which are substantially UV opaque, are of interest for use with the present invention.

In the instance where the bottle assembly is made from material, such as polyethylene, which is not substantially UV opaque, the sterilising apparatus of the present invention may further comprise a shroud, the shroud being extendable for shrouding the bottle. In this way, any potentially damaging UV light escaping through the polyethylene bottle is prevented from reaching the eyes of a user by the use of the external shroud. The shroud extendable in any suitable manner for example it may be telescopically extendible or may be collapsible by folding upon itself.

A sterilising apparatus according to the present invention may further comprise engaging means that automatically engage the housing on the bottle assembly when the sterilising apparatus is fitted to the bottle assembly. For example this may be a clip-on arrangement. This allows for easy attachment and detachment.

It is desirable that a sterilising apparatus of the invention has an integral power source for the UV light source, for example a rechargeable battery. This means that no electrical connection is required for sterilisation to take place. In some instances, it may be desirable for the user that the device of the invention can be used when connected to an electrical source, such as by means of a plug and mains socket.

The device of the invention may comprise a resiliently flexible tab which flexes upon attachment of the steriliser to the bottle assembly to activate the UV light source. This is a simple arrangement which allows switching on and off of the device. For example the flexible tab may engage a (micro) switch which activates the UV light source.

The housing desirably comprises at least one closed chamber that separates any electronic control or power source from the housing. This ensures that there is no contamination of the bottle from working components such as electronics/battery etc.

It is desirable that the UV light source is an elongate bulb that emits UV light along its length. It is desirable that the bulb is at least about 20 mm, for example at least about 25 mm, such as at least about 30 mm, desirably at least about 35 mm, such as about 40-50 mm long. Such lengths are suitable as the bulb extends a substantial way into the bottle. The UV light source may comprise any suitable source including a mercury vapour bulb or a xenon vapour bulb.

It may be desirable to provide a UV-penetrable protective cover for the UV light source. This can avoid contamination of the light source and contamination of any part of the bottle assembly that touches the bulb. The cover will still allow for sterilisation of the bottle assembly. If desirable the cover may be disposable, e.g. a releasably detachable cover.

It is desirable that the sterilising apparatus further comprises a detachable cover for the housing. This means that when the device is not attached to a bottle assembly the cover can protect the housing. The cover detaches sufficiently from the housing to allow the housing to be fitted to a bottle assembly.

In one aspect, the detachable cover may be dimensioned to accommodate a bottle. It is desirable that the detachable cover may be adapted to block any UV light that passes through the bottle. The detachable cover may include at least one retaining member for retaining the bottle in position for sterilisation thereof, wherein the retaining member may be in the form of a seat for the bottle. In the present aspect of the invention, the apparatus may further comprise a safety mechanism to prevent emission of UV light for sterilising the bottle if the cover is not attached. The purpose of this safety mechanism is to ensure that a user will not inadvertently activate the UV light source without having a protective cover in place.

In certain embodiments of the invention, certain conditions may have to be met in order to provide a failsafe mechanism so that the retina of a user are not exposed to UV radiation. Such conditions may be a failsafe condition of the device that before any UV source is activatable for sterilisation of the bottle and/or the teat that one or more of the conditions (i) the cover must be (correctly) in place; (ii) the bottle is correctly in position (for example with the bulb extending into the bottle but without touching it); (iii) the cover of the enclosed chamber is closed (for the appropriate embodiments); and (iv) the teat is correctly in position. Desirably the device of the invention is configured so that all of the conditions must be met before sterilisation is activatable. Sterilisation, for example a sterilisation cycle, may commence automatically once the required conditions are met.

The present invention also relates to a method of sterilising a feeding bottle assembly for a baby comprising the steps of:
  providing a feeding bottle assembly comprising:
    a feeding bottle, a top end and a base end, the top end having an open neck;
  providing a sterilising apparatus of the present invention,
  attaching the sterilising apparatus to the feeding bottle; and
  irradiating the bottle with sufficient UV light to sterilise the bottle.

The method of the invention also works where the feeding bottle assembly comprises a teat-retaining ring for sealing engaging a teat to the open neck of the bottle and the method comprises attaching the sterilising apparatus to the teat-retaining ring.

The method of the invention includes a method where the feeding bottle assembly comprises a teat and the method comprises the step of placing the teat in the bottle before irradiating the bottle with sufficient UV light to sterilise the bottle (and teat). The method of the invention includes a method where the feeding bottle assembly comprises a teat and the method comprises the step of placing the teat in an enclosed chamber of the apparatus and irradiating the bottle and teat with sufficient UV light to sterilise the bottle and the teat. This is very desirable as both the teat and the interior of the bottle are sterilised. A complete bottle assembly for feeding is thus sterilised in one go. In addition the interior of that part of any retaining ring that is present that comes into contact with liquid in the bottle may also be sterilised in this process.

The present invention extends to a sterilising apparatus substantially as herein described, with reference to, and as illustrated in, the accompanying drawings. The present invention extends to a method of sterilising a feeding bottle assembly as herein described, with reference to, and as illustrated in, the accompanying drawings.

BRIEF DESCRIPTION OF THE DRAWINGS

Additional features and advantages of the present invention are described in, and will be apparent from, the detailed description of the invention and from the drawings in which:

FIGS. 4A to 4D illustrate the apparatus of the present invention being mounted on different types of baby feeding bottles.

FIGS. 10A-E illustrate a further embodiment of the apparatus of the present invention in which: FIG. 10A illustrates a rear view of the apparatus in a closed configuration with a cover in place; FIG. 10B illustrates a front view thereof; FIG. 10C is a perspective view of the apparatus; FIG. 10D is a (top) plan view thereof; and FIG. 10E illustrates a perspective view of the apparatus which has been inverted and with the cover removed to reveal a UV light source.

FIGS. 11A and 11B illustrate a schematic representation of the apparatus of FIGS. 10A-10E mounted on a charging cradle and directly attached to a power source, respectively.

FIG. 12A illustrates a schematic representation of the apparatus of FIGS. 10A-10E with a shroud attached thereto and with a teat and an additional UV light source positioned in an upper chamber thereof. FIGS. 12B and 12C illustrate a schematic representation of the steps for mounting an apparatus of FIG. 12A on a baby feeding bottle, with a teat situated inside the upper chamber of the apparatus, and the shroud deployed to block UV light transmitted through the bottle.

FIG. 14A illustrates a cross-sectional view of the apparatus of FIGS. 10A-10E in a configuration for storage thereof with a shroud in a retracted configuration; FIG. 14B illustrates the apparatus of in a working configuration with a teat (in outline) positioned in the upper chamber and attached to a baby feeding bottle and with the shroud deployed.

FIGS. 15A and 15B illustrate the apparatus of the FIGS. 10A-10E mounted on different types of baby feeding bottles and with the shroud deployed.

FIGS. 19A and 19B illustrate a schematic representation of the apparatus of FIGS. 18A-18F directly attached to a power source and mounted on a charging cradle, respectively.

DETAILED DESCRIPTION OF THE DRAWINGS

It should be readily apparent to one of ordinary skill in the art that the examples disclosed herein below represent generalised examples only, and that other arrangements are possible and are embraced by the present invention.

Figure 1:
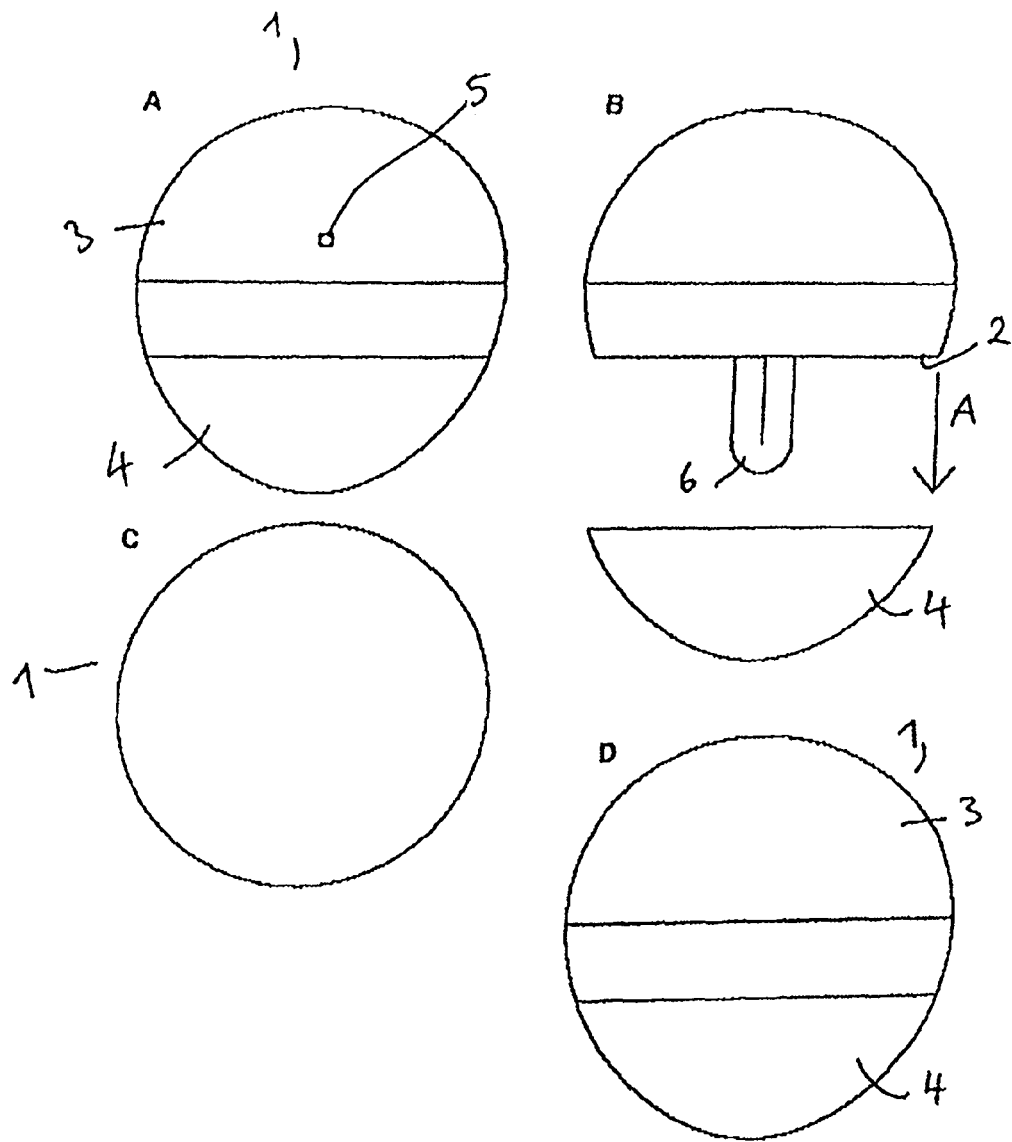
FIG. 1A illustrates a schematic of the apparatus of the present invention in a closed configuration with a cover in place.
FIG. 1B illustrates the apparatus of the present invention with the cover removed (in the direction of arrow A) to reveal a UV light source.
FIG. 1C illustrates a (top) plan view of the apparatus of the present invention.
FIG. 1D illustrates a rear view of the apparatus of the present invention.
FIGS. 1E and 1F show the self-righting nature of a device of the invention.
Figure 1E:
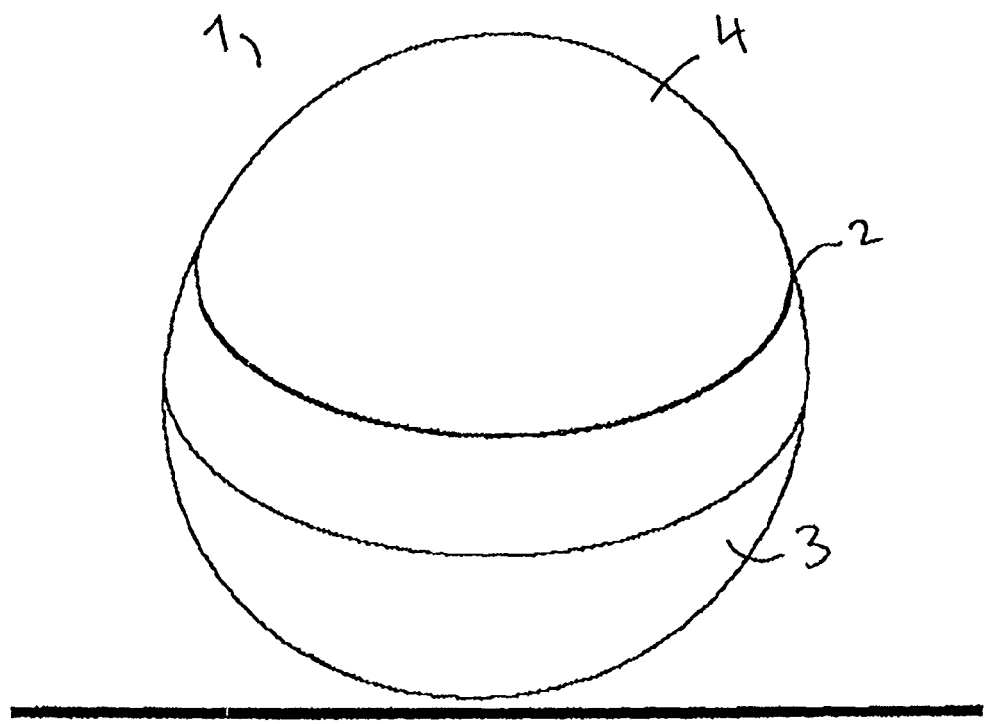
Figure 1F:
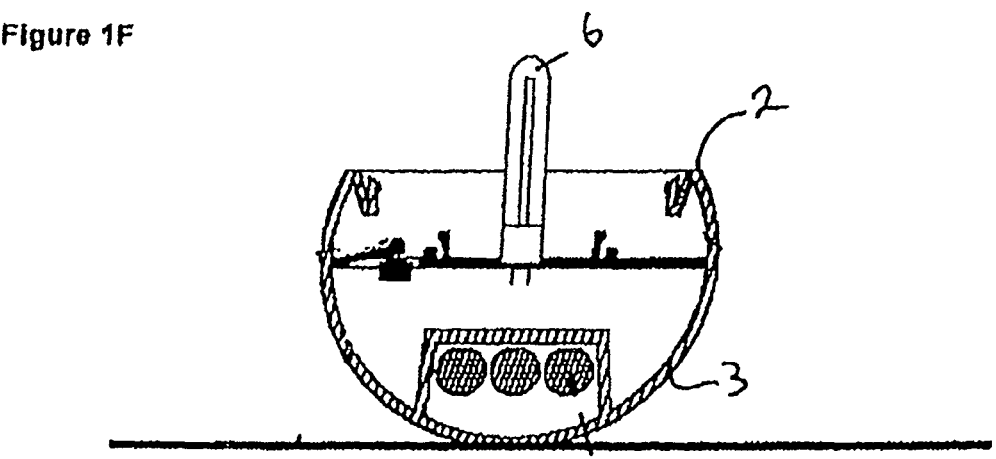

In FIG. 1 there is illustrated: FIG. 1A a rear view in a closed configuration with a cover in place, FIG. 1B an open configuration with the cover removed, FIG. 1C a top plan view and FIG. 1D a rear view of a portable sterilising apparatus according to the present invention. FIGS. 1E and 1F show the rest (righted) position of the self-righting arrangement of the device. Whenever left down on a surface the device of the invention will always self-right to the position shown in FIGS. 1E and 1F. The apparatus is for use with open-necked containers, and preferably with feeding bottles such as baby feeding bottles. The apparatus is generally indicated by the reference numeral 1, and is generally elliptical in shape. The apparatus 1 comprises a housing 2 which is adapted to attach to and sit on the top of a bottle assembly, an upper section 3 which forms at least one chamber for holding operational components of the device, such as electronics/battery and a removable cover 4. The upper section 3 of the housing 2 comprises a port 5. The port 5 is a charging point for charging the device of the invention. The device of the invention is shaped and weighted to always take up the position shown in FIGS. 1E and 1F, that is, sitting with the housing 2 (and bulb 6) held in an upright position.

As illustrated in FIG. 1B, the removable cover 4 is detachable from the upper section 3 by hand using manual force applied in the direction of arrow A. The cover detaches to reveal a UV light source in the form of a UV bulb 6. The UV bulb 6 is removably connected to the upper section 3 of the housing 2. The cover is detached from the housing 2 for attaching the device of the invention to bottles for sterilisation of bottles.

Figure 2:
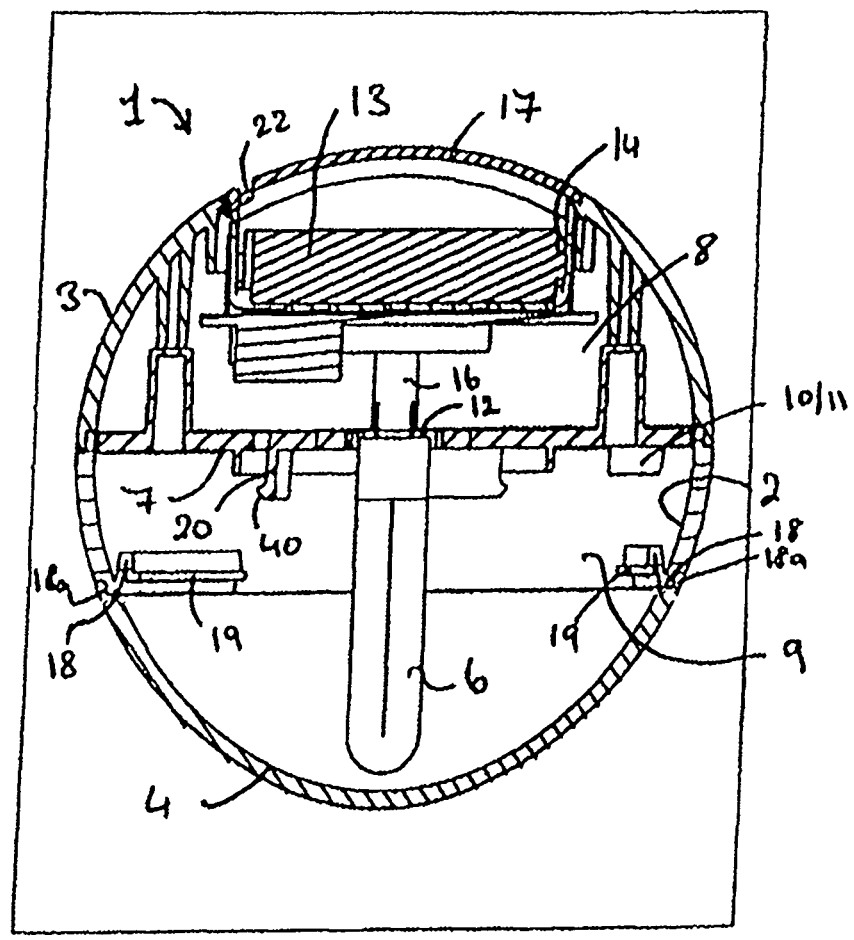
FIG. 2 illustrates a schematic representation of a cross-sectional view of the apparatus of the present invention.

As illustrated in FIG. 2, the UV bulb 6 is held to a support by a socket 12. The support takes the form of a dividing wall 7 that separates the upper section 3 into an upper chamber 8 and an open-mouthed lower chamber 9 that defines a housing 2.

The upper chamber 8 includes a battery dock 14 for a battery 13 and electronic controls 15. The battery 13 and controls 15 together control and power operation of the UV bulb 6, and will be explained in more detail later. The port 5 allows the battery 13 to be charged and also the option of powering the device utilising mains electricity if the battery 13 is not present or is flat.

The support wall 7 of the upper section 3 has attached thereto and positioned to one side in the housing 2 a flexible tab 10 (best seen in FIG. 4). The flexible tab 10 is moveable so as to be able to contact a micro switch 11 (best seen in FIG. 4). The micro switch 11 switches on and off power to electronic controls 15 and is biased towards the "off" position.

When the flexible tab 10 comes in contact with the micro switch 11, the micro switch 11 is in the "on" position (see FIG. 4B and FIG. 4D) and activates the UV light source 6. When the flexible tab 10 is not in contact with the micro switch 11, the UV light source 6 remains deactivated (see FIG. 4A and FIG. 4C). This means that in FIGS. 4B and 4D the device 1 is automatically activated for sterilising the bottles 30 to which it is attached.

In one preferred aspect of the present invention, a suitable control such as a timer control in the electronic controls 15 deactivates the UV light source when a pre-determined sterilisation protocol is completed. It will be appreciated that the controls can be programmed to also vary other parameters, if desired, such as intensity etc.

FIGS. 3 and 4 show a device of the invention fitted to feeding bottles of two different types.

Figure 3A:
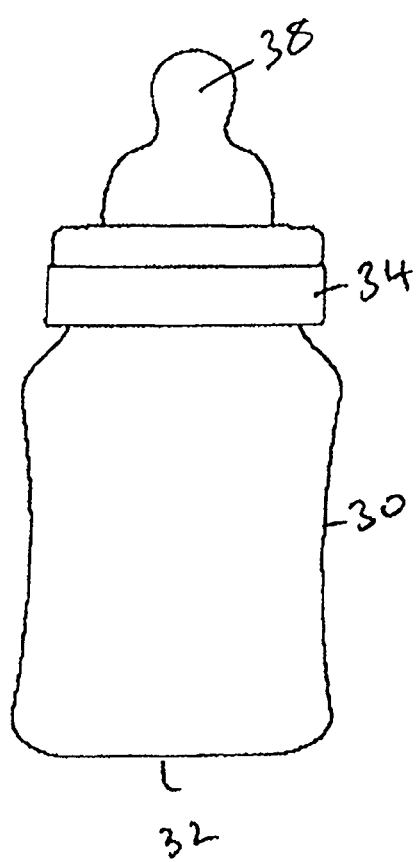
FIG. 3A illustrates a schematic representation of a baby feeding bottle with a teat and ring attached.
Figure 3B:
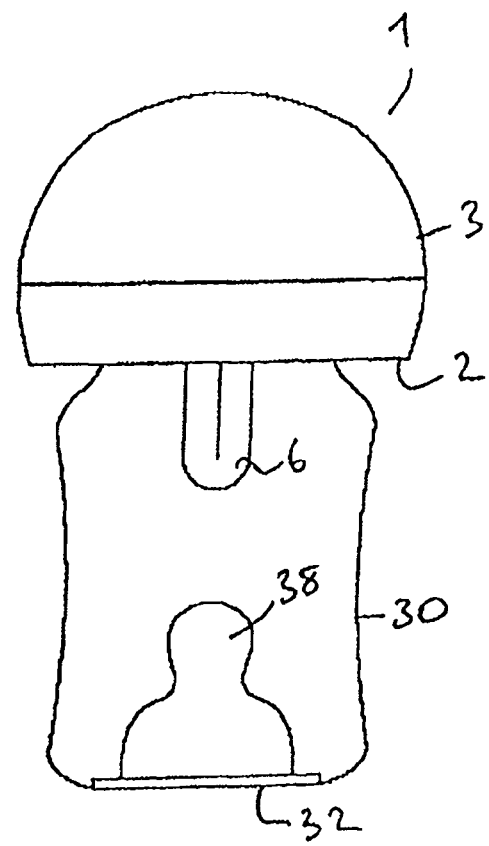
FIG. 3B illustrates a schematic representation of the apparatus of the present invention mounted on the baby feeding bottle, with the teat situated inside the bottle and resting on the bottle base.

A bottle 30 is shown in FIG. 3A and FIG. 4A and FIG. 4B. The bottle 30 has a top end 31 and a base end 32. The top end 31 has an open neck 33. A teat-retaining collar or ring 34 has been fitted to the bottle by conventional means such as reciprocal threading. The teat-retaining ring 34 has an open centre and an inner lip 35 on the ring 34 is for engaging in a groove in a teat 38. The ring 34 is for sealingly engaging a teat 38 on the bottle as shown in the assembly of FIG. 3A. Before sterilisation the teat 38 is removed or placed within the bottle 30 where it may be sterilised by the device of the invention (see FIG. 3B). It will be appreciated that an inner side 37 of the retaining ring 34 will also be irradiated and thus sterilised.

The apparatus 1 is capable of being held in one hand and is simply placed over and mounted on the top of the bottle 30. The UV bulb 6 is inserted through the open neck 33 of the bottle 30. The apparatus 1 is pushed in the direction of arrow B to lock the container with suitable engagement means. Suitable engagement means include those for gripping about the exterior of the bottle neck or retaining ring or alternatively or additionally gripping an interior of the bottle neck or retaining ring.

Suitable engaging means include resilient grips 19 (FIG. 4C-D) formed on an inside wall of the housing 2 and/or resilient grips 40 (FIG. 4A-B) located centrally within the housing 2 to grip an interior of the ring.

The grips 40 are desirably connected to and are projecting from the dividing wall 7 either side of the bulb 6. The bottle 30 can easily be removed by applying manual pressure to disengage it from its attached position.

The apparatus 1 of the present invention may include a collar 20 extending down from the support wall 7 into the lower chamber 9. The collar may include engagement means in the form of grips 40. The collar 20 surrounds the point where the bulb 6 is held by in its socket 12 on the dividing wall 7. A seal between the open neck 33 and/or retaining ring 34 of the bottle 30 and the dividing wall 7 is formed.

It will be appreciated that when the device of the invention is engaged with the bottle 30 the tab 10 abuts an upper surface 36 of the retaining ring 34. This pushes the tab 10 (upwardly) to the position shown in FIGS. 4B and 4D. This in turn contacts the micro switch 11, to move it to its "on" position to activate the UV light source and emit light from bulb 6. It will be appreciated that the device of the invention can also attach directly to the bottle, (that is where no retaining ring 34 is present). In such a case a rim 25 on the top end 31 of the bottle will abut the tab 10 to activate the UV light. In such a case the engaging means will be arranged to grip an exterior or interior of the bottle neck.

It will be appreciated that the apparatus 1 of the invention is very compact and is arranged to sit on top of the bottle while the sterilisation process proceeds. The apparatus 1 will mount to the neck 33 of wide and narrow-necked baby feeding bottles.

The bottle 30 shown in FIGS. 4C and 4D has a different exterior shape to that of FIGS. 4A and 4B. It also has a substantially more pronounced shoulder 31 on which the neck 33 sits. The retaining ring 34, while of a different shape to that of FIGS. 4A and 4B, has the same function. It has an inner lip 35 for retaining a teat 38 and an upper surface 36 which the tab 10 can abut (as shown in FIG. 4D) to activate the light source.

Removal of the apparatus 1 can be achieved by manual pressure to disengage it from its attached position. If the sterilisation cycle is not complete then removal of the device will cause the micro switch 11 to return to its off position thus interrupting the cycle.

In one desired aspect of the present invention, the pre-determined sterilisation protocol comprises exposing the inner surface of the container to a cycle of UV radiation for between about 1 minute and about 20 minutes, preferably between about 2 minutes and about 15 minutes, more preferably between about 4 minutes and about 12 minutes, and even more preferably between about 8 minutes and about 10 minutes. In some embodiments of the invention (see below) it is possible to achieve sufficient sterilisation in less than 1 minute, for example less than 50 seconds, such as less than 40 seconds, including less than 30 seconds and indeed less than 20 seconds. In one arrangement sufficient sterilisation is achieved in less than 15 seconds for example within about 10 seconds.

The UV bulb 6 receives power from battery 13 in the battery receiving dock 14 via electronic controls 15. Any suitable controls can be employed. The bulb 6 is connected to the electronic controls 15 by connection 16. The micro switch 11 is an actuating means for turning the UV bulb 6 on or off. As explained above, the UV light source is activated only when pressure is exerted from the flexible tab 10 on to the micro switch 11.

The UV light source may be of any type known to those in the industry that is capable of sterilising surfaces. The UV light source typically comprises a tube lamp manufactured from glass. In one aspect of the present invention, the UV light source emits UV light having a wavelength in the range of 100 nm to 280 nm, which is commonly called UV-type C (UV-C) radiation. In one aspect of the present invention, the bulb 6 may be covered by a protective cover such as a protective sheath, through which UV radiation can penetrate, to prevent accidental breakage of the bulb 6. The protective cover will prevent any contact with the bulb surface, which is desirable to prevent contamination by the bulb and/or the bulb being fouled.

A cover panel in the form of a flap 17 is situated at the apex of, and is flush with, the upper section 3 of the apparatus 1. The flap 17 has a notch 22 that permits the user to open the flap 17 and access the battery 13 docked in the battery dock 14. The port 5 is located below the flap 17. It will be understood by those skilled in the art that the user may also use one or more non-rechargeable batteries to provide power to the UV light source.

As shown in FIG. 2 there is provided within the housing 2 an engaging means in the form of a rim 18. The engagement means may alternatively comprise spaced apart individual portions intermittently placed around the circumference of the housing 2. The engaging means interengages with a corresponding engaging means comprising a rim 18a on the cover 4. The two rims click-fit together to secure the cover 4 to the apparatus 1.

If desired it is possible to construct the engaging means for engaging the cover on the device to also function to secure the device to a bottle to be sterilised.

For baby feeding bottles manufactured from polycarbonate, the UV radiation from the UV light source cannot pass through this material. Therefore, there is no risk to the user from exposure to UV radiation. Furthermore, the teat for the bottle can be placed inside the bottle and sterilised simultaneously with the bottle. For bottles constructed of other materials that allow UV light through to any substantial extent a shroud may be employed for example as described below.

Figure 5:
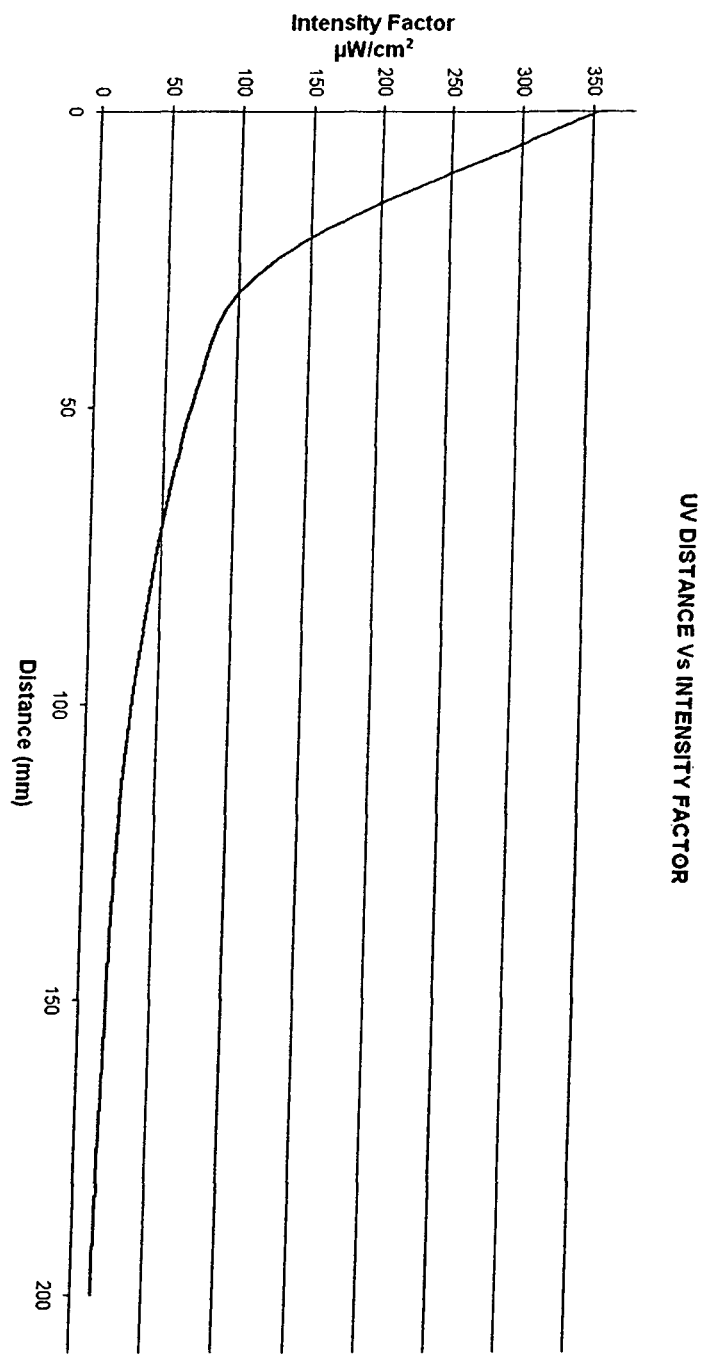
FIG. 5 illustrates a measure of the intensity factor of the UV radiation ($\mu W/cm^2$) vs. distance (millimetres (mm)) from the radiation source.

The energy required to kill microorganisms is dependent on the UV light source intensity factor (intensity by Watt rating) and exposure time (seconds) to said energy. This energy is measured in microwatt seconds per square centimetre ($\mu$Watt Seconds/cm$^2$). UV radiation is emitted predominately perpendicular to the surface of the lamp. As such, the intensity factor of UV radiation acting on a surface at different distances from a UV light source was determined and plotted on a graph as illustrated in FIG. 5. Recommended dosages of UV radiation for an average 90% kill/inactivation of most bacteria and virus range from 2,000 to 8,000 $\mu$Watt Seconds/cm$^2$. The device of the invention achieves an at least 90% average kill/inactivation of bacteria/virsues. It provides sufficent intensity and duration of UV light to achieve this. Desirably the device of the invention provides UV irradiation that is a multiple of the minimum dose to achieve this 90% kill/inactivation. For example it is desirable that the dose deliverable during a sterilisation cycle is at least 2 times, suitably at least 3 times, for example at least 4 times, such as at least 8 times, desirably at least 10 times that required to achieve an at least 90% average kill/inactivation.

EXAMPLES

Part I

Figure 6A:
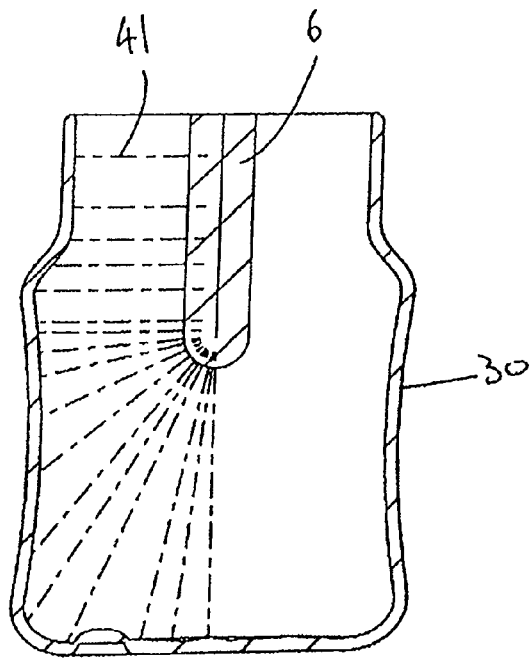
FIG. 6A illustrates a schematic representation of a cross-sectional view of a Philips "Avent AirFlex" 125 ml Bottle with a UV light source positioned in the neck thereof and the direction of UV radiation emitted from the UV light source in the bottle.
Figure 6B:
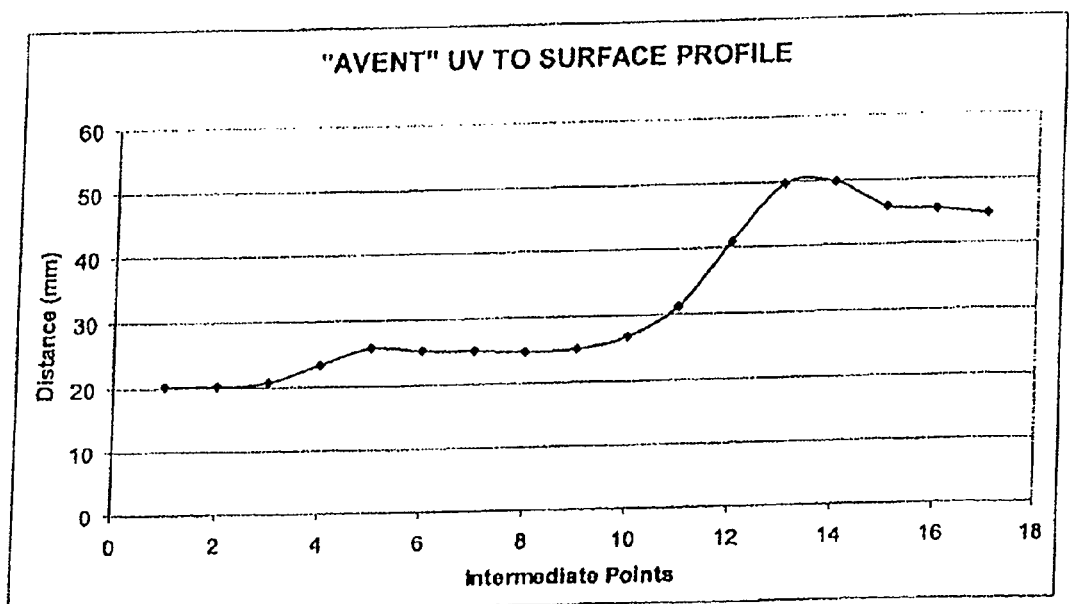
FIG. 6B is a graph of Distance (mm) vs. Intermediate Points, or bulb to surface distance profile, wherein the intermediate points represent the various points on the inner surface of the bottle at which the UV radiation intensity is measured.
Figure 7A:
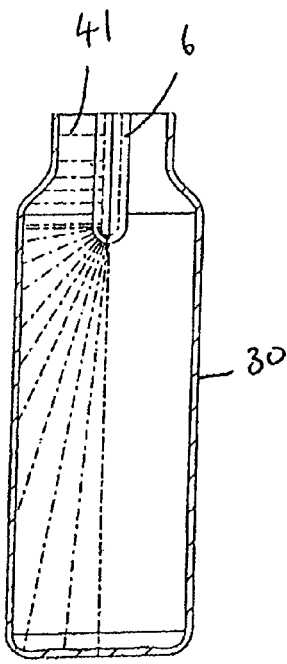
FIG. 7A illustrates a schematic representation of a cross-sectional view of a Dr Brown's Natural Flow® 240 ml Bottle with a UV light source positioned in the neck thereof and the direction of UV radiation emitted from the UV light source in the bottle.
Figure 7B:
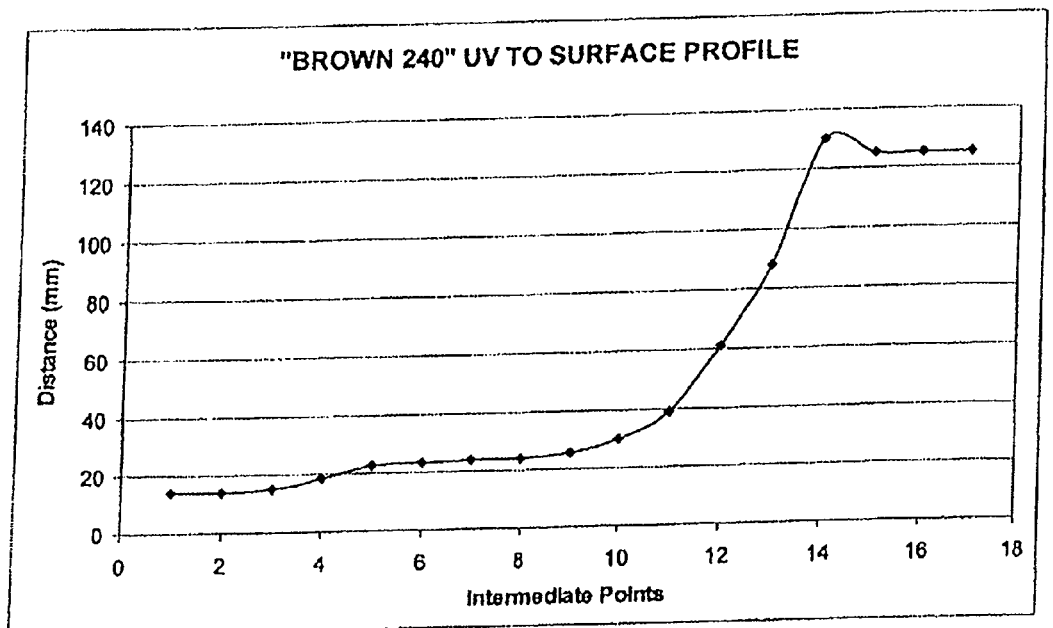
FIG. 7B is a graph of Distance (mm) vs. Intermediate Points, or bulb to surface distance profile, wherein the intermediate points represent the various points on the inner surface of the bottle at which the UV radiation intensity is measured.
Figure 8A:
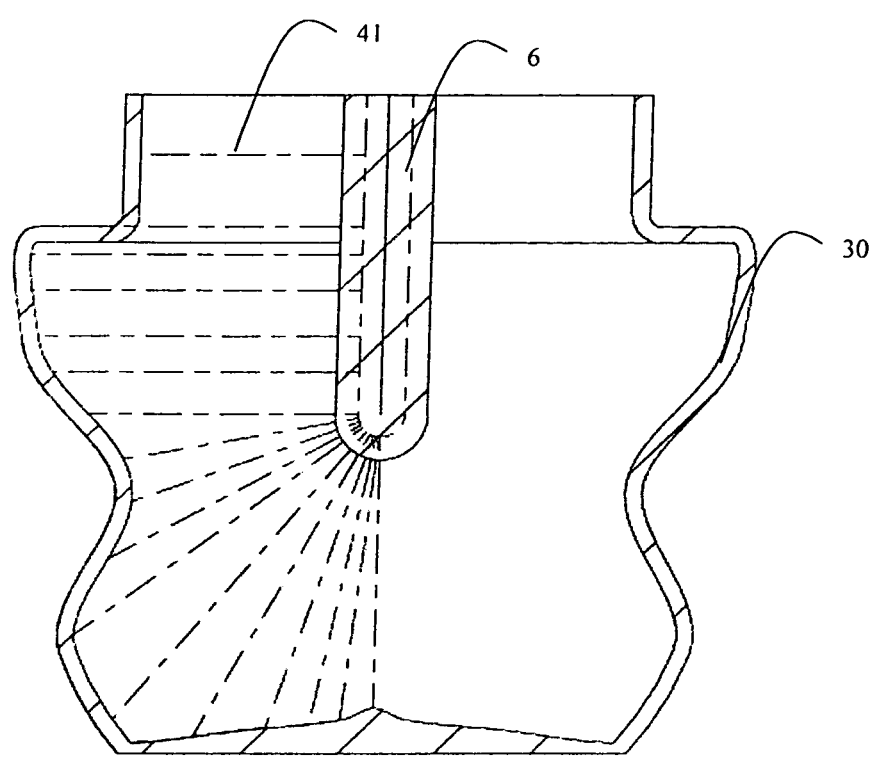
FIG. 8A illustrates a schematic representation of a cross-sectional view of a Tommee Tippee® 150 ml Bottle with a UV light source positioned in the neck thereof and the direction of UV radiation emitted from the UV light source in the bottle.
Figure 8B:
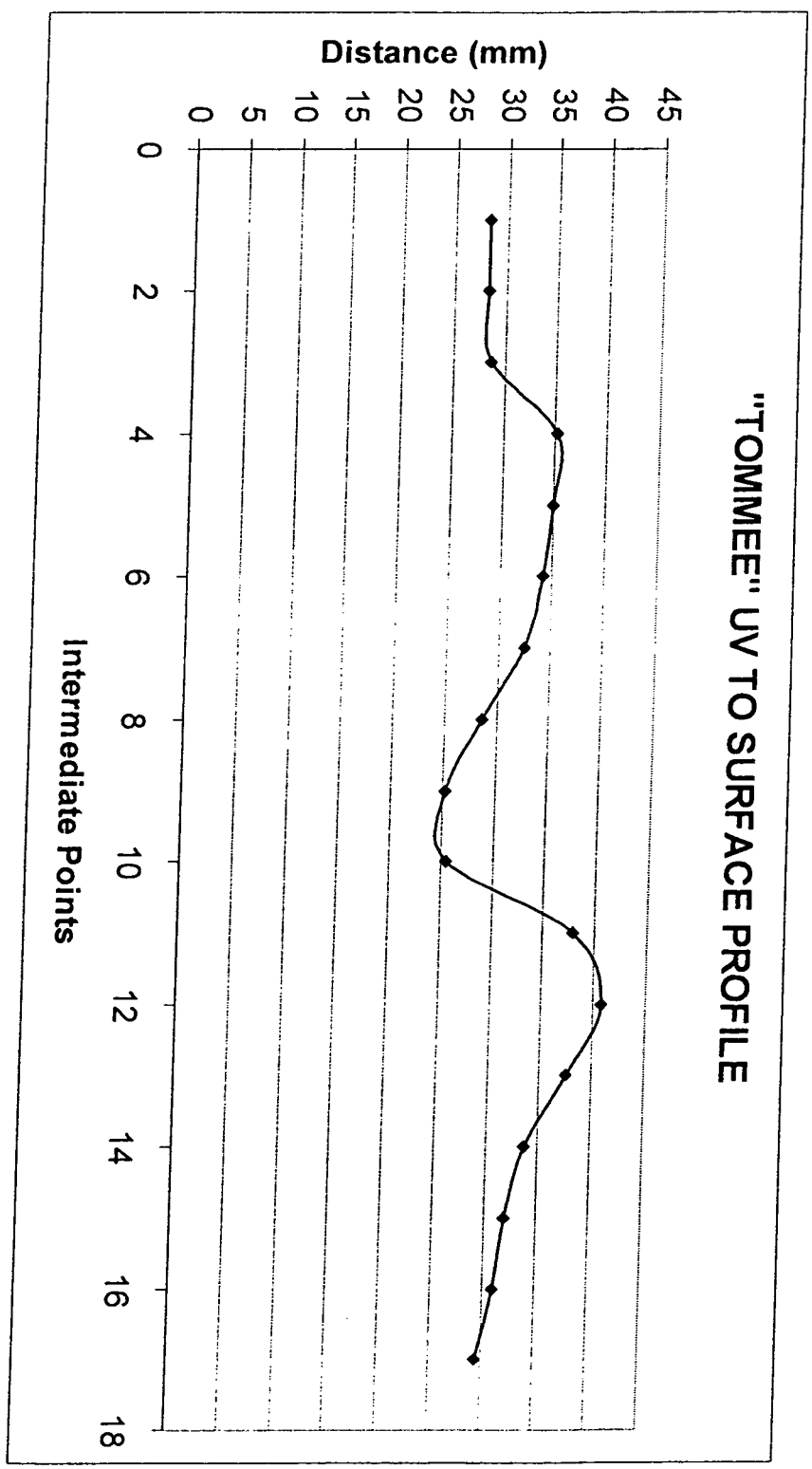
FIG. 8B is a graph of Distance (mm) vs. Intermediate Points, or bulb to surface distance profile, wherein the intermediate points represent the various points on the inner surface of the bottle at which the UV radiation intensity is measured.

The following are examples of the energy at the surface of a number of commercially available baby feeding bottles. The intensity factor of the UV radiation at the inner surface of a particular bottle at different distances from the UV source (bulb 6) is measured against the graph of FIG. 5. The distances from the bulb 6 to various points on the inner surface of the bottle 30 are tabulated below. The lines 41 highlighted in FIGS. 6A, 7A, and 8A correspond to the distances measured, and are plotted on a graph of Distance (mm) versus Intermediate points (17 distances corresponding to a particular point on the inner surface of the bottle 30) as shown in FIG. 6B, 7B, and 8B, respectively. The distance points represent the various contours of the inner surface of the particular bottle 30 being tested. A 40 mm long, 3 Watt (W) low-pressure mercury bulb with a light intensity rating of 1.1 at 1 m ($\mu$W/cm$^2$), and an exposure time/cycle of 5 minutes was used for each bottle. The dosage ($\mu$Wseconds/cm$^2$) is calculated by multiplying the intensity of the UV radiation at various points on the inner surface of the bottle 30 by the exposure time (seconds).

Example 1

Philips "Avent AirFlex" 125 ml Bottle—Overall Dimensions of 88 mm (Height)×61 mm (Width)

Table 1 below demonstrates that, even at the furthest distance from the UV light source to the inner surface of the bottle 30, the dosage provided by the apparatus 1 of the present invention in a Philips "Avent Airflex" baby feeding bottle is at least 10-fold higher than the lowest dosage that is typically recommended for killing or inactivating 90% of known bacteria and viruses.

TABLE 1

| Point No. | Distance (mm) | Intensity factor | 3 W Lamp Rating of 1.1 Light Intensity at 1 m ($\mu$W/cm$^2$) | Intensity (Intensity factor × Lamp Rating) | Time (seconds) | Dosage ($\mu$Watt seconds/cm$^2$) |
|---|---|---|---|---|---|---|
| 1 | 20.3 | 157 | 1.1 | 172.7 | 300 | 51810 |
| 2 | 20.3 | 157 | 1.1 | 172.7 | 300 | 51810 |
| 3 | 20.707 | 155 | 1.1 | 170.5 | 300 | 51150 |
| 4 | 23.292 | 137 | 1.1 | 150.7 | 300 | 45210 |
| 5 | 25.784 | 122 | 1.1 | 134.2 | 300 | 40260 |
| 6 | 25.261 | 126 | 1.1 | 138.6 | 300 | 41580 |
| 7 | 25.071 | 127 | 1.1 | 139.7 | 300 | 41910 |
| 8 | 24.808 | 128 | 1.1 | 140.8 | 300 | 42240 |
| 9 | 25.053 | 126 | 1.1 | 138.6 | 300 | 41580 |
| 10 | 26.75 | 116 | 1.1 | 127.6 | 300 | 38280 |
| 11 | 31.21 | 97 | 1.1 | 106.7 | 300 | 32010 |
| 12 | 40.9 | 79 | 1.1 | 86.9 | 300 | 26070 |
| 13 | 49.7 | 70 | 1.1 | 77 | 300 | 23100 |
| 14 | 49.74 | 70 | 1.1 | 77 | 300 | 23100 |
| 15 | 45.9 | 74 | 1.1 | 81.4 | 300 | 24420 |
| 16 | 45.39 | 75 | 1.1 | 82.5 | 300 | 24750 |
| 17 | 44.6 | 75 | 1.1 | 82.5 | 300 | 24750 |

Please note:
Point No. 1-17 are referenced above for the X-axis plot in FIG. 6B

Example 2

Dr Brown's Natural Flow® 240 ml Bottle—Overall Dimensions of 167 mm (Height)×56.3 mm (Width)

Table 2 below demonstrates that, even at the furthest distance from the UV light source to the inner surface of the bottle, the dosage provided by the apparatus 1 of the present invention in a Dr. Brown's Natural Flow® baby feeding bottle is at least 3.4-fold higher than the lowest dosage that is typically recommended for killing or inactivating 90% of known bacteria and viruses.

TABLE 2

| Point No. | Distance (mm) | Intensity factor | 3 W Lamp Rating of 1.1 Light Intensity at 1 m (μW/cm²) | Intensity (Intensity Factor × Lamp Rating) | Time (seconds) | Dosage (μWatt seconds/cm²) |
|---|---|---|---|---|---|---|
| 1 | 13.875 | 237 | 1.1 | 260.7 | 300 | 78210 |
| 2 | 13.875 | 237 | 1.1 | 260.7 | 300 | 78210 |
| 3 | 14.86 | 205 | 1.1 | 225.5 | 300 | 67650 |
| 4 | 17.79 | 180 | 1.1 | 198 | 300 | 59400 |
| 5 | 21.88 | 145 | 1.1 | 159.5 | 300 | 47850 |
| 6 | 23.42 | 136 | 1.1 | 149.6 | 300 | 44880 |
| 7 | 23.73 | 136.5 | 1.1 | 150.15 | 300 | 45045 |
| 8 | 25.67 | 122 | 1.1 | 134.2 | 300 | 40260 |
| 9 | 29.906 | 102 | 1.1 | 112.2 | 300 | 33660 |
| 10 | 38 | 82 | 1.1 | 90.2 | 300 | 27060 |
| 11 | 47.35 | 71 | 1.1 | 78.1 | 300 | 23430 |
| 12 | 62.31 | 56 | 1.1 | 61.6 | 300 | 18480 |
| 13 | 90.08 | 37 | 1.1 | 40.7 | 300 | 12210 |
| 14 | 128.25 | 22 | 1.1 | 24.2 | 300 | 7260 |
| 15 | 126.59 | 23 | 1.1 | 25.3 | 300 | 7590 |
| 16 | 126 | 24 | 1.1 | 26.4 | 300 | 7920 |
| 17 | 126 | 24 | 1.1 | 26.4 | 300 | 7920 |

Please note:
Point No.s 1-17 are referenced above for the X-axis plot in FIG. 7B Example 3

Tommee Tippee® 150 ml Bottle—Overall Dimensions of 72 mm (Height)×77.5 mm (Width)

Table 3 below demonstrates that, even at the furthest distance from the UV light source to the inner surface of the bottle, the dosage provided by the apparatus 1 of the present invention in a Tommee Tippee® baby feeding bottle is at least 13-fold higher than the lowest dosage that is typically recommended for killing or inactivating 90% of known bacteria and viruses.

TABLE 3

| Point No. | Distance (mm) | Intensity Factor | 3 W Lamp Rating of 1.1 Light Intensity at 1 m (μW/cm²) | Intensity (Intensity Factor × Lamp Rating) | Time (seconds) | Dosage (μWatt seconds/cm²) |
|---|---|---|---|---|---|---|
| 1 | 28.24 | 109 | 1.1 | 119.9 | 300 | 35970 |
| 2 | 28.24 | 109 | 1.1 | 119.9 | 300 | 35970 |
| 3 | 28.62 | 108 | 1.1 | 118.8 | 300 | 35640 |
| 4 | 35.14 | 87 | 1.1 | 95.7 | 300 | 28710 |
| 5 | 34.92 | 87 | 1.1 | 95.7 | 300 | 28710 |
| 6 | 34.14 | 87 | 1.1 | 95.7 | 300 | 28710 |
| 7 | 32.53 | 93 | 1.1 | 102.3 | 300 | 30690 |
| 8 | 28.62 | 107 | 1.1 | 117.7 | 300 | 35310 |
| 9 | 25.21 | 125 | 1.1 | 137.5 | 300 | 41250 |
| 10 | 25.448 | 125 | 1.1 | 137.5 | 300 | 41250 |
| 11 | 37.83 | 83 | 1.1 | 91.3 | 300 | 27390 |
| 12 | 40.79 | 80 | 1.1 | 88 | 300 | 26400 |
| 13 | 37.49 | 83 | 1.1 | 91.3 | 300 | 27390 |
| 14 | 33.61 | 90 | 1.1 | 99 | 300 | 29700 |
| 15 | 31.88 | 97 | 1.1 | 106.7 | 300 | 32010 |
| 16 | 31.01 | 97 | 1.1 | 106.7 | 300 | 32010 |
| 17 | 29.5 | 103 | 1.1 | 113.3 | 300 | 33990 |

Figure 9:
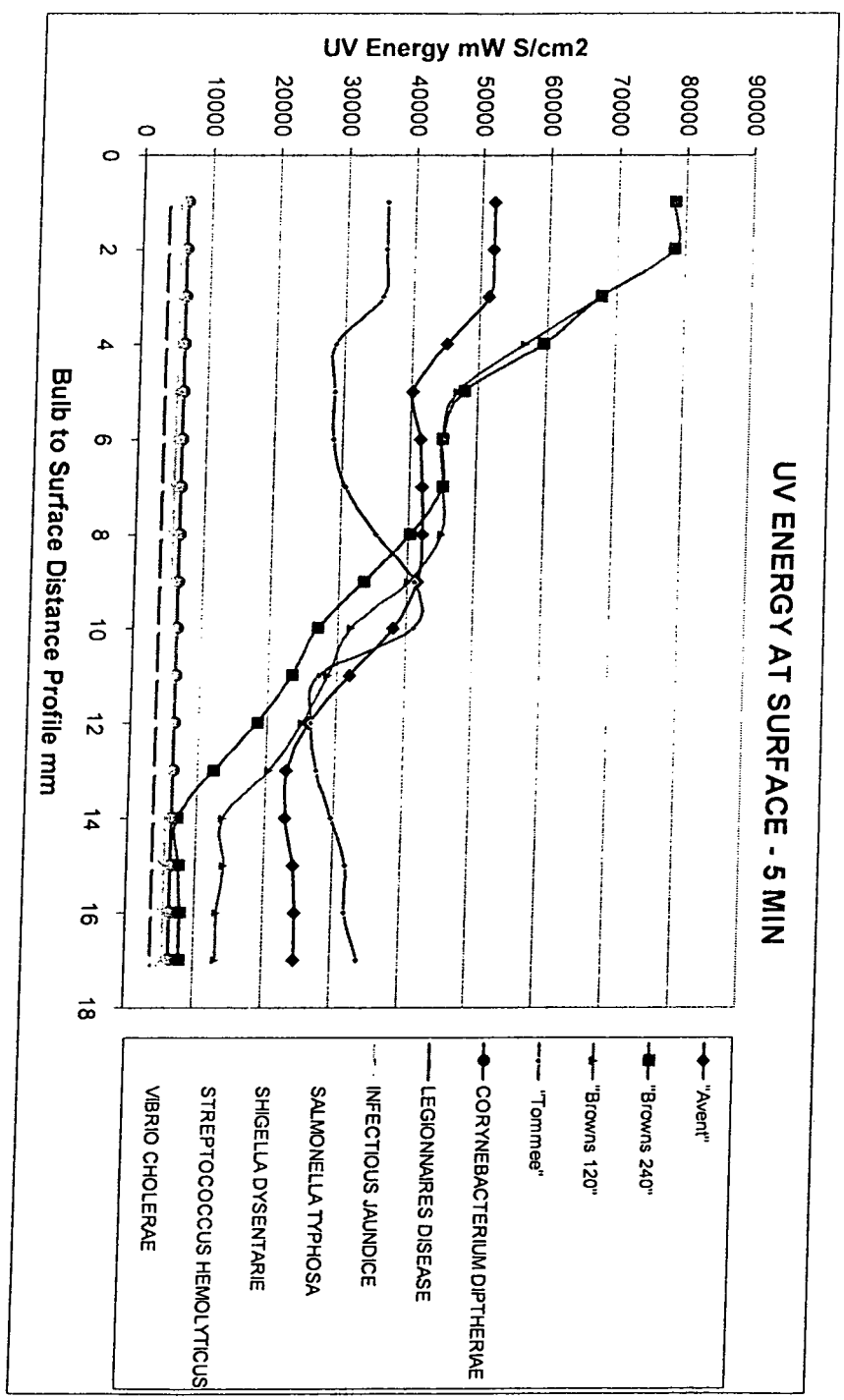
FIG. 9 is a graph of UV Energy (Dosage) ($\mu WS/cm^2$) vs. Intermediate Points (bulb to surface distance profile) illustrating the UV radiation energy achieved at the surface of a selection of commercially available baby feeding bottles and the energy (dosage) required to kill/inactivate a selection of microorganisms.
Figure 10:
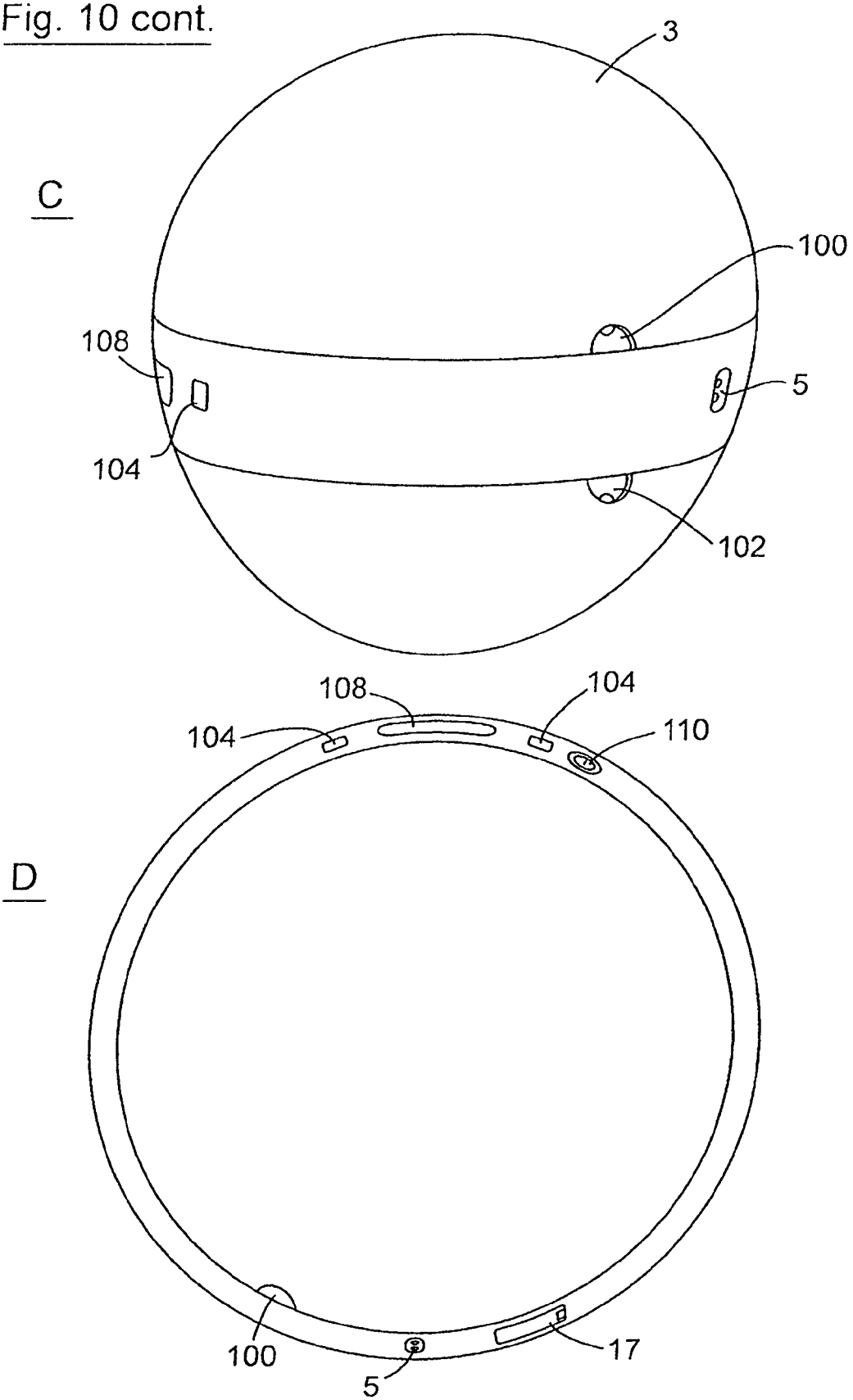
Figure 10:
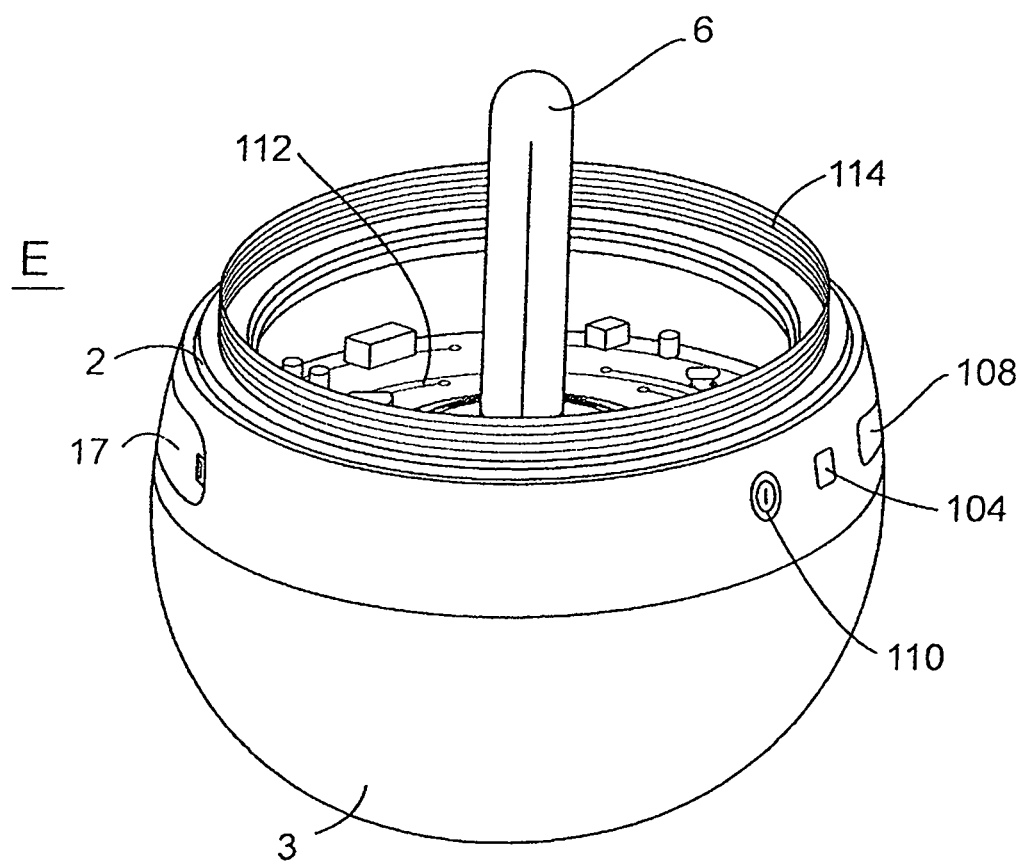
Figure 13:
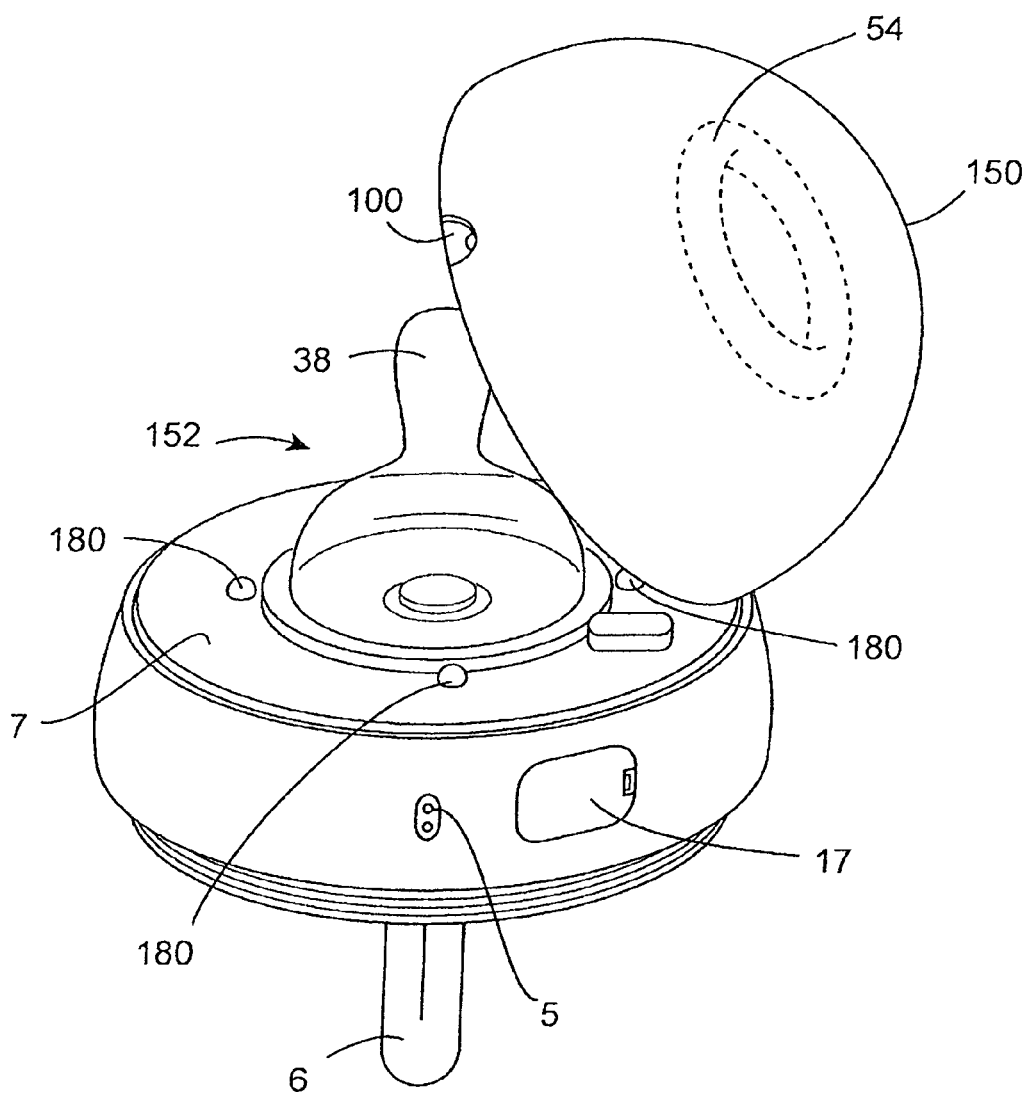
FIG. 13 illustrates an enlarged view of the apparatus of FIGS. 12A-C with a teat in position in the upper chamber thereof.

Please note:
Point No.s 1-17 are referenced above for the X-axis plot in FIG. 8B The graph illustrated in FIG. 9 is a plot of Intermediate Points (Bulb/UV to Surface Distance Profile) (x-axis) (Point No.s 1 to 17 from Tables 1 to 3, corresponding to Intermediate Points of the graphs of FIGS. 6B, 7B, and 8B, respectively) versus their corresponding dosage (Y-axis) (μWatt seconds/cm²) at the surface of the interior of the baby feeding bottles as per Examples 1 to 3. Further, the recommended dosage for killing or deactivating a range of microorganisms, for example, *Vibrio cholerae, Corynebacterium diptheriae, Legionella* bacteria causing Legionnaires disease, Infectious jaundice (known as Weil's disease, which is caused by *Leptospira interrogans* serogroup icterohaemorrhagiae), *Salmonella typhosa, Shigella dysentaire, Steptococcus hemolyticus,* are also plotted on the graph of FIG. 9. As can be seen, it is clearly evident that the energy emitted by the bulb 6 of the apparatus 1 at the inner surface of the bottle 30 is more than sufficient to kill/deactivate a range of microorganisms. It will be clearly understood by one skilled in the art that all microorganisms and viruses, which can be killed/deactivated by exposure to UV radiation with a wavelength of between 100 nm and 280 nm, are inherently included with the above examples.

Further embodiments are illustrated in FIG. 10 to FIG. 19. Corresponding features between apparatuses are represented by the same reference numerals. In FIGS. 10A and 10B a rear and front view in a closed configuration with a cover in place, respectively, FIGS. 10C and 10D a perspective and top (plan) view, respectively, and FIG. 10E an open configuration with the cover removed of a portable sterilising apparatus according to the present invention.

In FIG. 10A there is provided a port 5 and a flap 17 situated on the side of, and flush with, the upper section 3 of the apparatus 1. Latches 100,102 are located on the upper section 3 and cover 4, respectively. The latch 102 allows the user to remove the cover 4 for attachment to a bottle in the manner described for embodiments above. Latch 100 allows a part 130 of the upper section 3 in the form of a cover 150 (see FIG. 12A) to be opened. In FIG. 10B a timer 108 can be seen which allows the user to set the time for which the device emits UV light or for automated cycles displays the cycle time, for example by counting down from or counting up to a specific time. LED lights 106 indicate to the user when the programmed time has finished by colour change, turning off/on, changing intensity etc. In addition, the device may also have an aural indicator either in addition to or in place of LED lights 106. There is also provided an on/off switch 110 which provides the user with an option to turn the UV light sources on when the apparatus is attached to a baby feeding bottle. All the above features are clearly visible in FIGS. 10C and 10E.

As illustrated in FIG. 10E, the removable cover 4 is detachable from the upper section 3 by twisting off from a threaded portion 114 on the housing 2. The cover detaches to reveal a UV light source in the form of a UV bulb 6. The UV bulb 6 is removably connected to the upper section 3 of the housing 2. The cover is detached from the housing 2 for attaching the device of the invention to bottles for sterilisation of those bottles. There is also illustrated a circuit board 112 which is situated on the dividing wall 7 that separates the upper section 3 into the upper chamber 8 and the open-mouthed lower chamber 9 that defines the housing 2. The circuit board 112 directs power from the power source to the UV bulb. It is however desirable that the electronics are isolated, for example enclosed in an electronics chamber, as described previously.

As illustrated in FIG. 11A, a charging cradle 50 is provided to supply power to the apparatus 1. The cradle 50 acts a docking device within which the apparatus 1 sits. A plug 62 is inserted to power source 60 and is connected to the cradle 50 by a lead and connector 63 inserted into a port 51 on the cradle. An indicator light 52 and an aural alarm indicate to the user when the apparatus 1 is charged and/or ready for use. Alternatively, the apparatus 1 may be connected directly to the power source 60 by connecting the lead and connector 63 to the port 5 on the upper section 3, as shown in FIG. 11B. An additional UV light source, in the form of a UV bulb 54 is indicated in outline in the upper chamber 8 of upper section 3, and will be discussed in more detail below.

As illustrated in FIG. 12A, a lid 150 of the upper chamber 8 is hingedly or pivotally attached at point 66, which permits movement of the lid 150 from a closed position (indicated in dashed outline) to an open position in the direction of arrow K. The teat 38 is placed into an enclosed chamber 152 and the cover 150 is closed by movement in the direction of arrow J. The enclosed chamber desirably isolates the teat from other parts of the device. A ring-shaped UV bulb 54 is attached internally to the lid 150, and when the lid is lowered in the direction of arrow J, the UV bulb 54 encircles the teat 38. In addition, there is provided a shroud 80 which is attached at position 82 on the housing 2.

The surfaces of the apparatus within chamber 152 and/or the cover 150 may be coated with a reflective surface 72, which would allow the UV light to be reflected inside the upper chamber 8 when activated (see FIG. 14). The reflective surface 72 intensifies the strength of the UV energy, which reduces sterilisation time and allows the UV light to contact all surfaces of the teat 38. The reflective surface 72 comprises any material that will reflect UV light. Such materials may be applied by any suitable means including being coated or applied by vacuum plating.

When the teat 38 is placed in the enclosed chamber 152 within nubs 180, as illustrated in FIGS. 12A-12C, and FIG. 13, the lid 150 is lowered in the direction of arrow L, and the apparatus 1 is placed on top of a baby feeding bottle 30, and as described above for FIG. 4. The apparatus 1 when placed on top and is engaged with the baby feeding bottle 30, the bottle supports the apparatus 1. Once the device of the invention is engaged with the bottle 30, and the shroud 80 is lowered in the direction of arrows M (FIG. 12B) to enshroud the bottle. This blocks any harmful amount of UV light from escaping. It will be appreciated that the shroud is also retractable and desirably is releasable from a retracted position to the extended position. Desirably the shroud is automatically released from its retracted position when the bottle is mated to the apparatus. The shroud is constructed to be UV opaque and any suitable materials, including coatings, may be employed for that purpose. As above, the shroud may be internally reflective. The shroud shown folds up upon itself (and expands) in an accordion type arrangement, though it will be appreciated that other mechanisms such as a telescopic arrangement could be employed. The UV light sources 6 and 54 are activated (in a manner described above for FIG. 4 and below for FIG. 14) and UV light is emitted. The placement of the teat 38 inside the upper chamber 8 and engagement with the bottle 30 allows the user to sterilise both the teat and bottle simultaneously. Desirably UV activation is prevented by a detection system that will not operate light source 6 until the bottle 30 is correctly in place and further optionally until the shroud is deployed to cover the bottle. It is also desirable that light source 54 is not activatable until the teat 38 is in place and/or the cover 150 is closed. Once however one or more of these conditions is met, sterilisation of the bottle and/or the teat may begin automatically. FIG. 12C shows light being emitted to sterilise both the teat and the bottle.

As illustrated in FIG. 14A, the aspects of the apparatus 1 is similar to that described for FIG. 2 but with the addition of the UV bulb 54, shroud 80 and reflective surface 72. The battery 13 is attached to the dividing wall 7 facing the open-mouthed lower chamber 9. The battery is connected to the UV bulb 54 by a connection 142. The UV bulb 54 is attached to the lid 150 by connection means 140. One skilled in the art will understand that any connection means known in the art would be suitable to attach the UV bulb 54 to the lid 150. The shroud 80 is connected to the underside of the housing 2 at points 82 and is maintained in a retracted position, indicated by arrows Q, by the cover 4 when the cover 4 is in place.

The shroud 80 may be constructed from any flexible, yet durable material selected from the group comprising rubber, plastic, and textiles. The shroud 80 may be extended like a bellows to enclose a baby feeding bottle when attached to the device of the present invention (see FIGS. 14B, 15A, 15B). Another suitable arrangement is where the shroud is made from a collapsible tubular material such as for example a collapsible tube reinforced with rings such as wire rings. Such collapsible tubular materials are often used as a flexible ducting for example as a vent hose on a electrically powered clothes dryer or on an extractor fan. As mentioned above a failsafe condition of the device will mean it will not be activatable when attached to a bottle unless the shroud 80 is extended to cover the bottle. A sensor may be employed for detecting the position of the shroud. Once in a fully extended position, the shroud 80 which then permits the activation of the UV bulbs 6 and 54.

In use, as illustrated in FIG. 14B and as described above for FIG. 4B, when the device of the invention is engaged with the bottle 30, the tab 10 abuts an upper surface 36 of the retaining ring 34. The retaining ring 34 has an inner lip 35 for retaining the teat 38 and an upper surface 36 which the tab 10 can abut. This pushes the tab 10 upwardly to the position shown in FIG. 14B (and also FIGS. 4B and 4D). This in turn contacts the micro switch 11, to move it to its "on" position to activate the UV light source and emit light from bulb 6 and bulb 54 (indicated by the small dashed arrows in the upper chamber 8 and in the bottle 30). It will be appreciated that the device of the invention can also attach directly to the bottle, (that is where no retaining ring 34 is present). In such a case a rim 25 on the top end 31 of the bottle will abut the tab 10 to activate the UV light. In such a case the engaging means will be arranged to grip an exterior or interior of the bottle neck.

Although baby feeding bottles are constructed primarily from polycarbonate, which adequately prevents UV light from escaping from the bottle when sterilised, bottle manufacturers are now manufacturing bottles from polyethylene due to concerns with bishpenol A leaching from bottles manufactured from polycarbonate. However, polyethylene does not prevent UV light from escaping and is not therefore substantially UV opaque. Therefore, in order to protect a user from the harmful effects of UV radiation on the retina, the shroud 80 is extended downward in the direction of arrow R from the underside of the housing 2 (see FIG. 14B).

FIGS. 15A and 15B illustrate the device (in use with the broken arrows indicating UV emission) of the present invention connected to two different baby feeding bottles with teat 38 in the chamber 152 and the shroud 80 deployed in an extended position to cover the bottle 30. The bottles 30 and the means to connect the device thereto are as described above for FIGS. 4A-4D.

Figure 16:
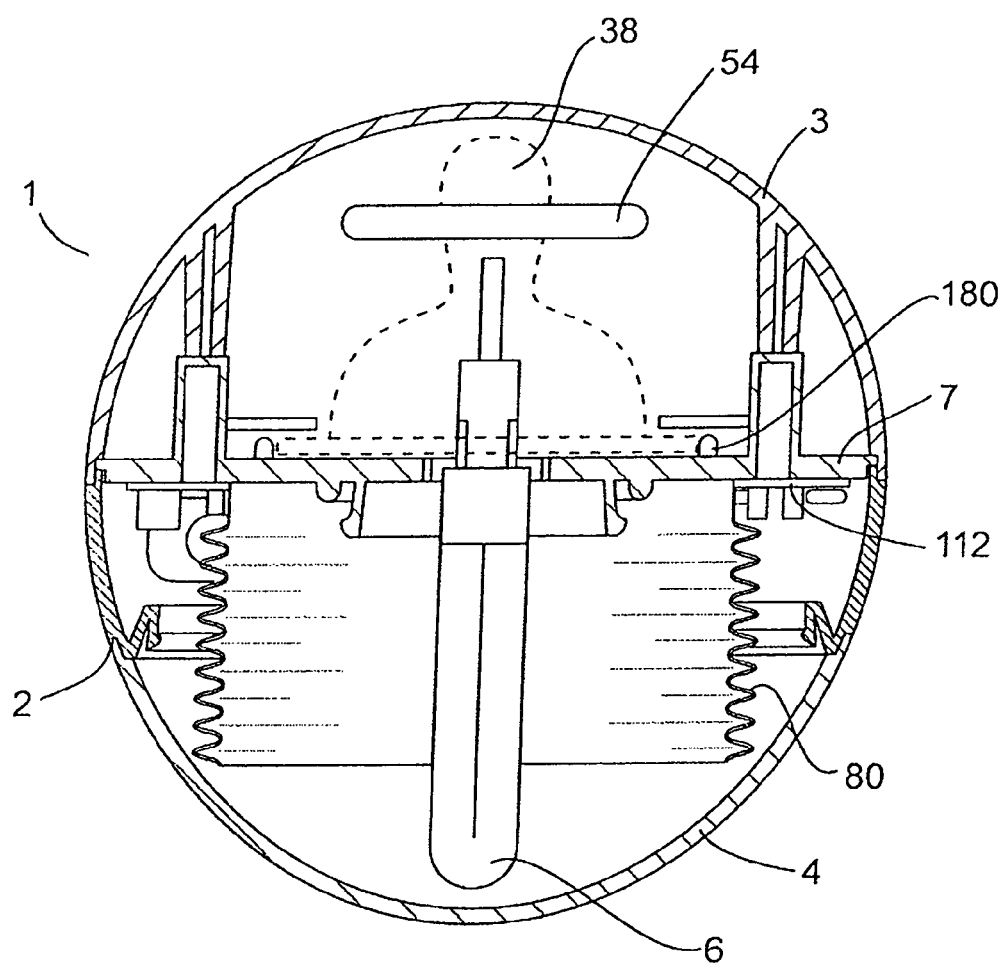
FIG. 16 illustrates a further embodiment of the apparatus of FIG. 14A where the shroud is attached to a dividing wall of the upper section.

An alternative position of the shroud 80 is illustrated in FIG. 16. Rather than being connected at points 82 on the underside of the housing 2 as illustrated in FIGS. 14 and 15, the shroud 80 may also be attached to the underside of the dividing wall 7 in the open-mouthed chamber 9.

Figure 17:
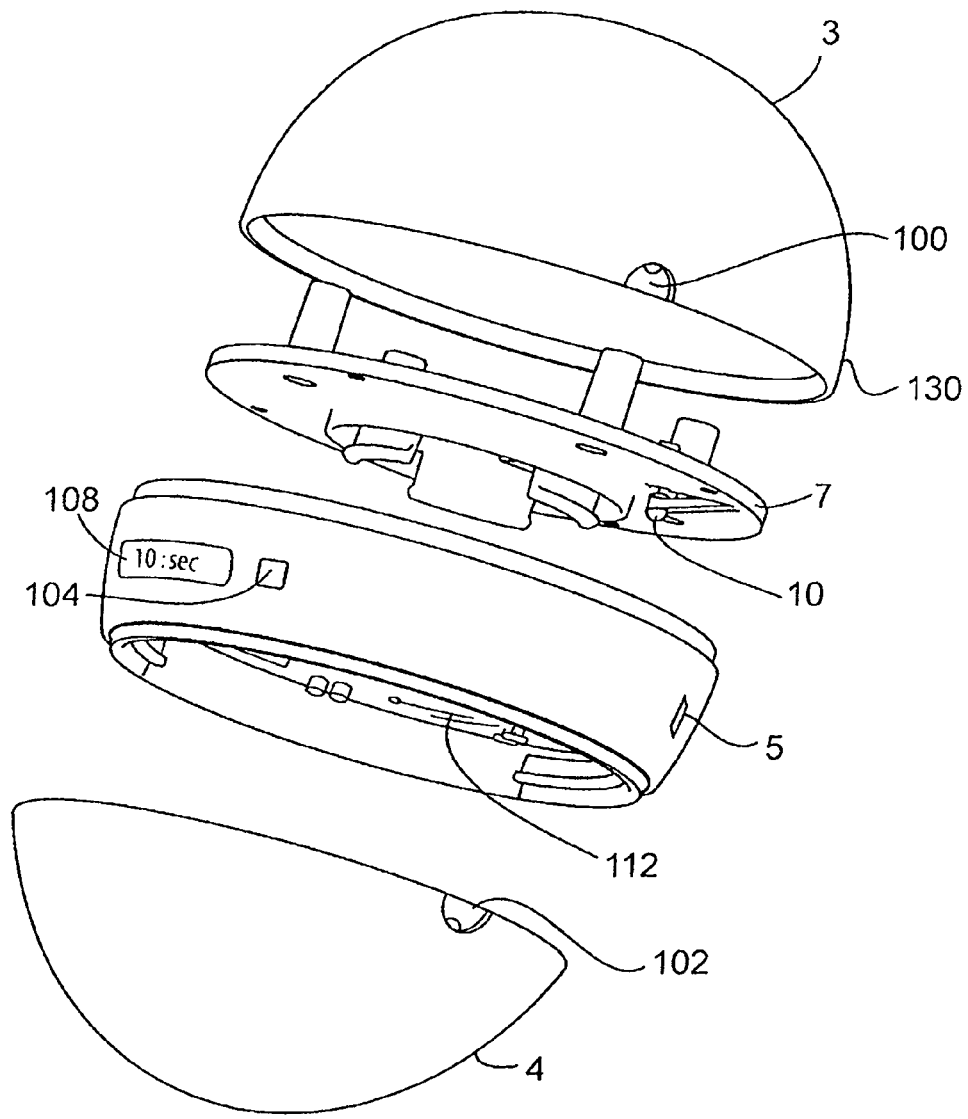
FIG. 17 illustrates an exploded view of the apparatus of FIGS. 10A-10E.

An exploded view of the device of the present invention is illustrated in FIG. 17.

Figure 18:
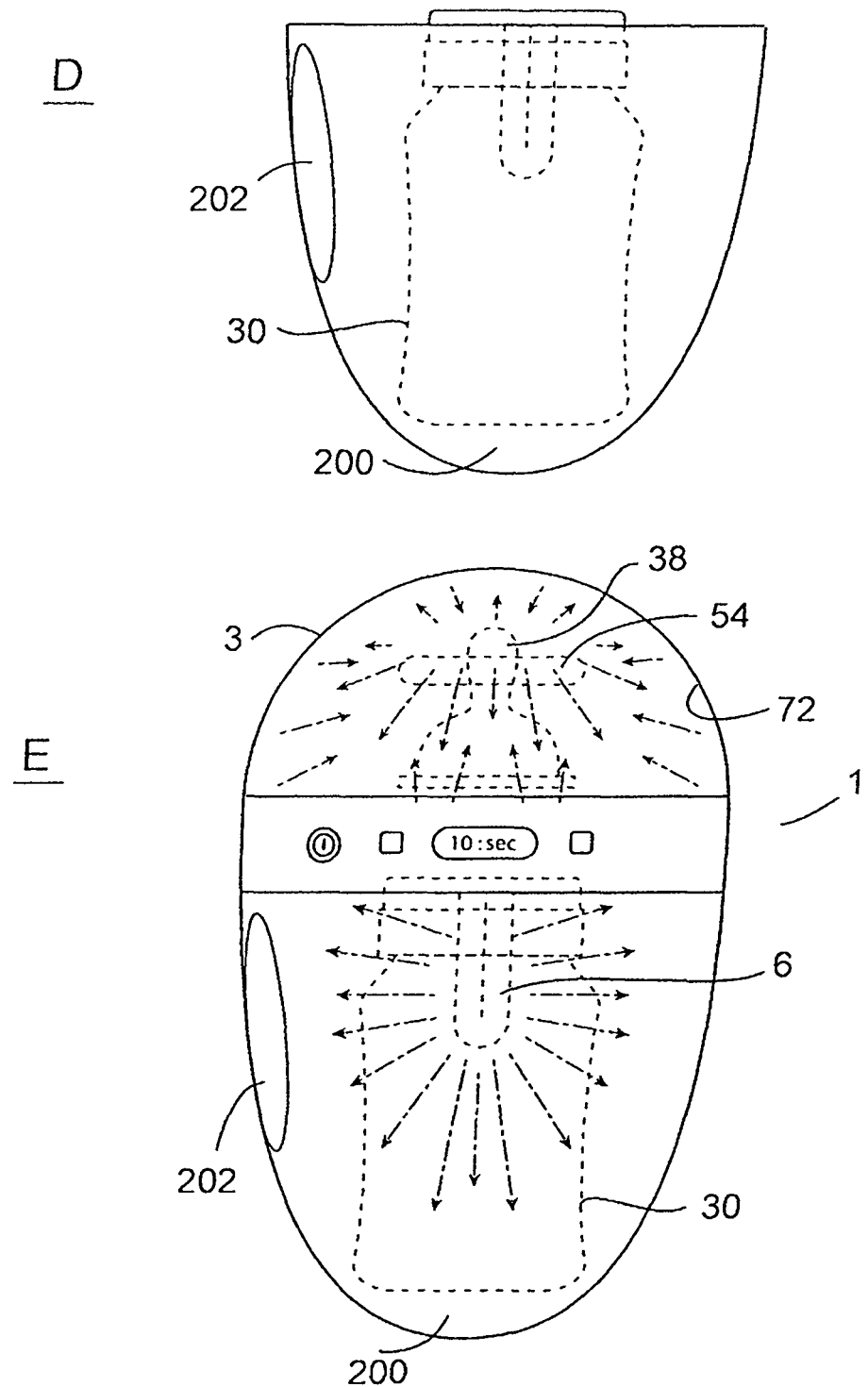
FIG. 18A to 18F illustrate schematic representation of a further embodiment of the present invention, where the device is adapted to accommodate a baby feeding bottle.

A further embodiment of the device of the present invention is illustrated in FIGS. 18 and 19. As illustrated in FIG. 18A there is provided an apparatus 1 having an upper section 3 as described above for FIG. 10 and a cover 200 within which a baby feeding bottle 30 can be accommodated. The cover 200 is an elongated version of the cover 4 described above for FIGS. 1 to 17. On one side of the cover 200 is a flat portion 202. The flat portion 202 prevents the apparatus 1 from rolling when placed on a surface, as illustrated in FIG. 18C. In use, the bottle 30 is placed inside the cover 200 in the direction of arrows T, where it rests on a supporting member in the form of a retaining seat 204 (as shown in FIG. 18B in cross section, and FIG. 18E as an outline). The apparatus 1 is attached to the bottle 30 in the usual manner as described above for sterilising the bottle and a teat. Once the upper section 3 is attached to the bottle 30 and connected to the cover 200, the UV bulbs 6 and 54 emit UV light, as shown in FIG. 18F, and sterilise both the bottle 30 and teat 38. It can be a failsafe condition of the device that before any UV source is activatable for sterilisation of the bottle and/or the teat that one or more of the conditions (i) the cover 200 must be (correctly) in place; (ii) the bottle is correctly in position (with the bulb extending into the bottle but without touching it); (iii) the cover 130 is closed; and (iv) the teat is correctly in position. Desirably the device of the invention is configured so that all of the conditions must be met before sterilisation is activatable. Sterilisation, for example a sterilisation cycle, may commence automatically once the required conditions are met.

The apparatus 1 of FIG. 18 can be connected to a cradle 50 as described above for FIG. 11, and as illustrated in FIG. 19B. The cradle 50 acts a docking device within which the apparatus 1 sits (FIG. 19B). Alternatively, the apparatus 1 may be connected directly to the power source 60 by connecting the lead and connector 63 to the port 5 on the upper section 3, as shown in FIG. 19A.

EXAMPLES

Part II

The following are examples determining the effective UV germicidal lamp exposure times. Initial organisms used for the tests to determine exposure times were: *Staphylococcus aureus*; *Streptococcus mutans*; *Enterococcus hirae*; *Escherichia coli*; and *Pseudomonas aeroginosa*.

The protocols for bacteria counts/survival were those used as standards in the industry. In this instance, cultures were grown to mid-exponential phase in appropriate broth at 37° C. Cultures were centrifuged at 10000 g for 5 min at 4° C. (Beckman), washed once, and suspended in saline (0.85% NaCl) at a density of $2 \times 10^6$ ml$^{-1}$ (based on prior count). Aliquots were transferred to a sterile bottle (1-10 ml). The aliquots in the bottle were exposed to UV light at room temperature. The UV lamp was measured as emitting at a wavelength of 254 nm. The UV lamp was held firmly in a clamp of a bench stand and the lamp and bottle were covered during the exposure period. A switch and timer were used to assign time periods of exposure, for example, 0, 10, 20, 30, 40, and 60 seconds (0 seconds acts as a control). The lamp was positioned identically for each experiment. After each exposure, 100 µl ($2 \times 10^5$ cells) aliquots were removed and spread on appropriate agar plates. The plates were cultured overnight at 37° C. and colonies, if any, were counted and recorded. All materials that bacterial cells are in contact with (centrifuge tubes etc) were sterile. Data will be presented as % bacterial survival (mean±SE) against time and UV dose.

For milk treatment experiments, the following protocols were followed:

Protocol 1
Sterile bottle filled with 180 ml of fresh full milk.
Incubated at room temperature for 30 minutes
100 µl of milk dilutions (neat, 1:10, 1:100 and 1:1000) plated in duplicate.
100 ml sterile water used to rinse the bottle
100 µl rinse water dilutions (neat, 1:10, 1:100 and 1:1000) plated in duplicate
Swabs from the bottle and neck were also taken
All plates were incubated at 32° C. for 48 hours.

Protocol 2
200 ml of fresh milk was incubated in a sterile bottle at room temperature for 30 minutes.
Following incubation a neat, 1:10, 1:100 and 1:1000 dilution was prepared and 100 µl was plated in duplicate.
The milk was discarded and the bottle was treated with the UV lamp for 10, 20, 30, 40, 50, 60, 90, 120 and 500 seconds containing rinse water.
After each UV exposure a sample of the rinse water was taken and 100 µl was plated in duplicate.
Plates were incubated at 32° C. for 48 hours.

Results

Figure 20A:
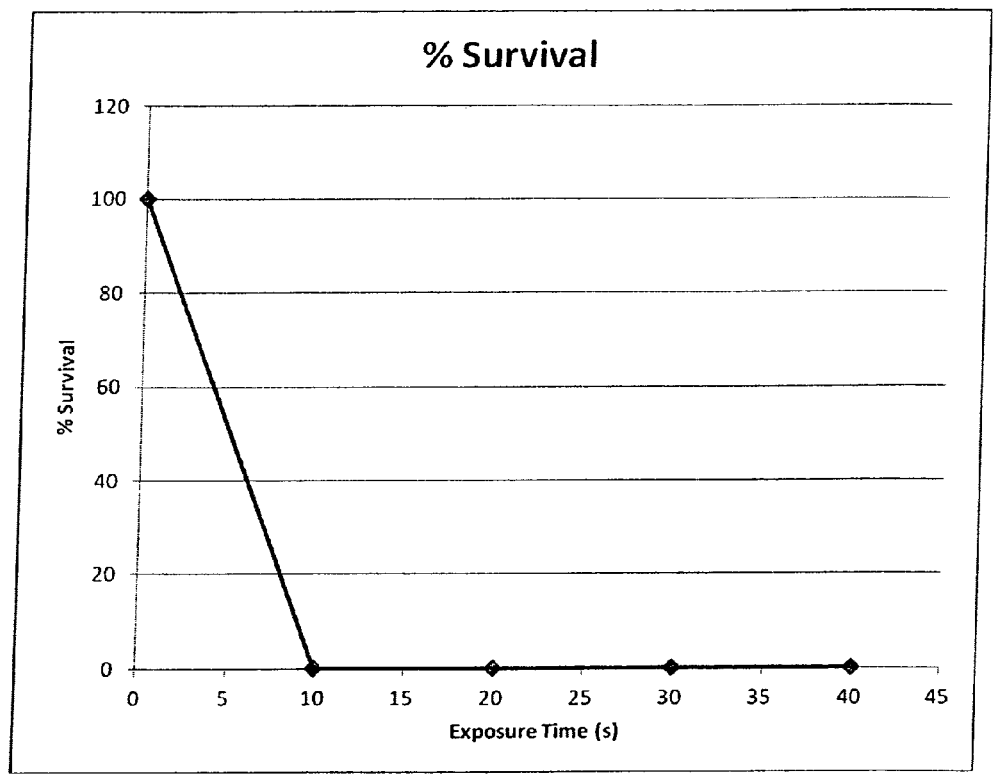
FIG. 20A to 20G are graphs of % (Bacterial) Survival vs. Time (seconds (s)) illustrating the time required to achieve a 100% kill rate of bacteria when a baby feeding bottle is exposed to UV radiation energy.
Figure 20B:
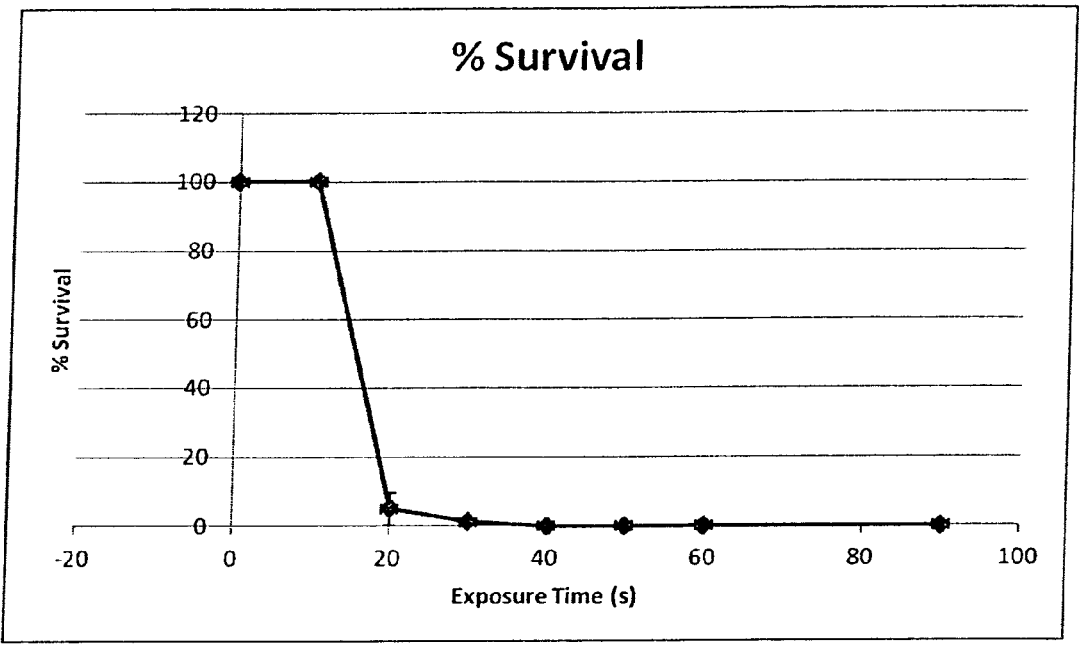
Figure 20C:
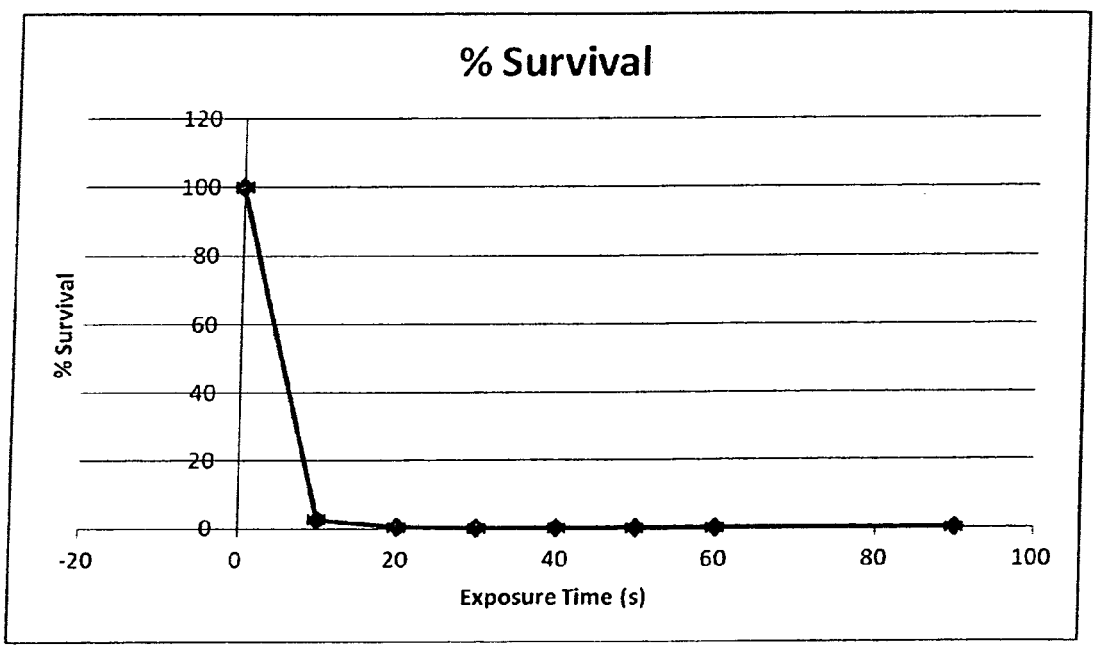
Figure 20D:
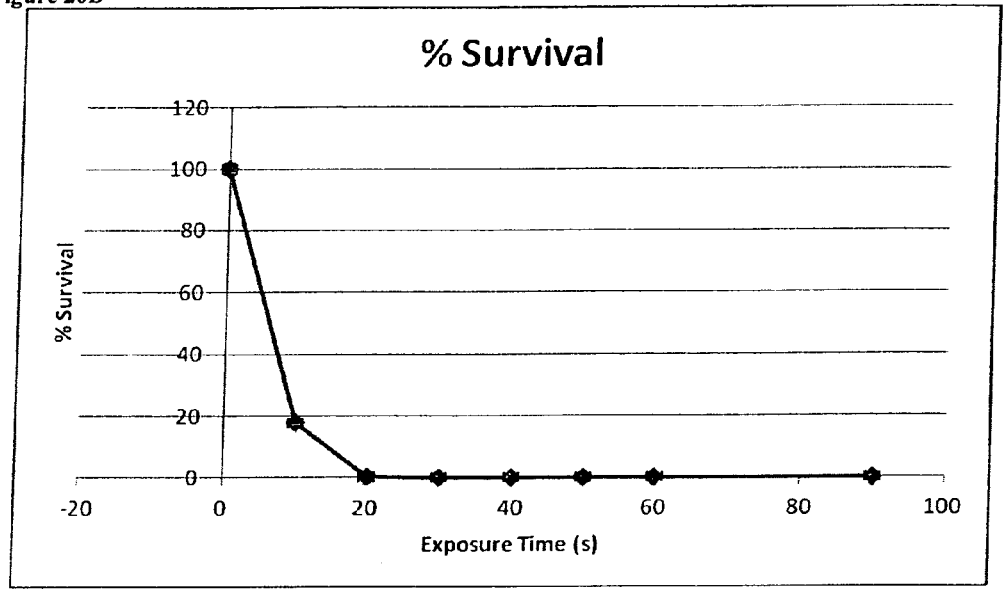
Figure 20E:
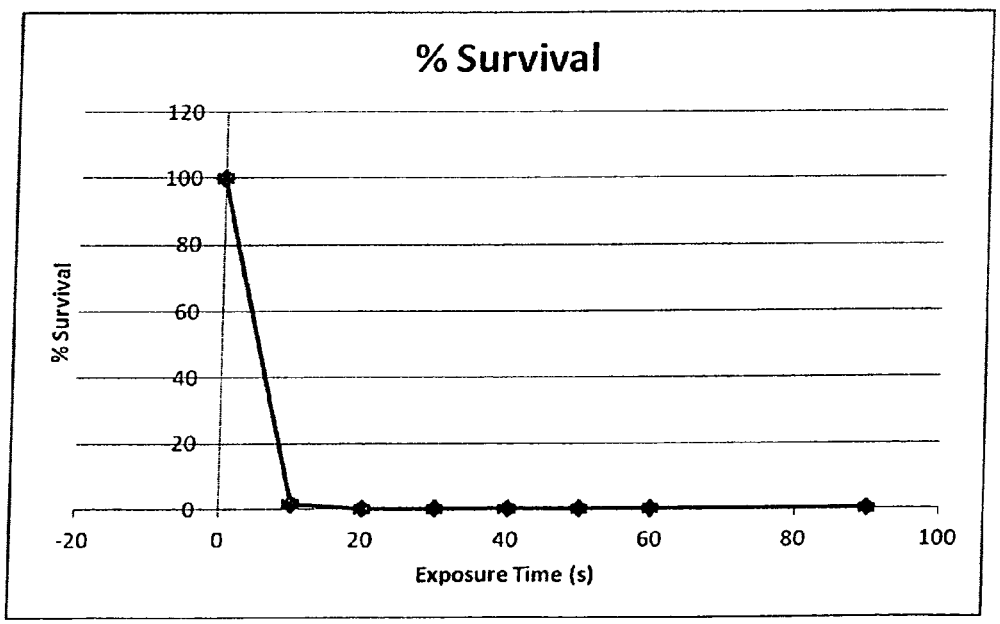
Figure 20F:
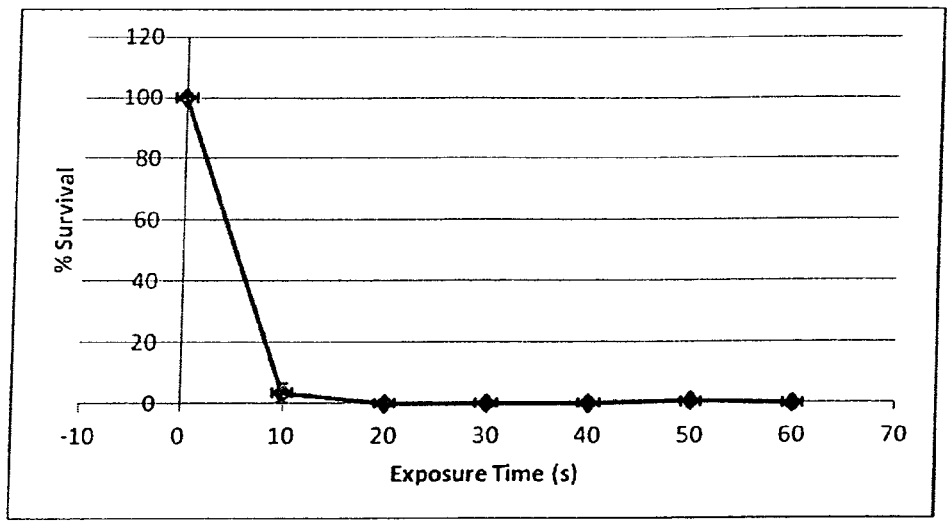
Figure 20G:
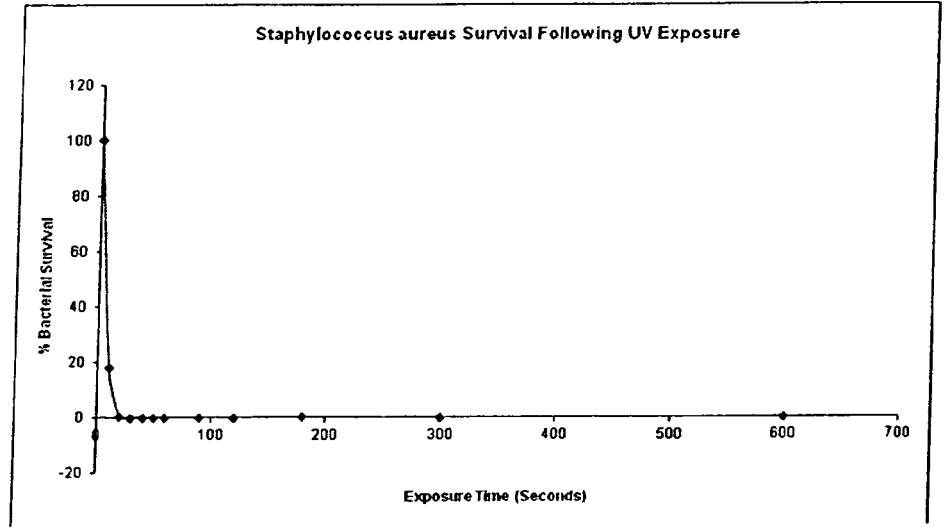

The results from the tests to determine the exposure time required for an effective 100% kill rate of bacteria on the surface of a bottle are presented in FIGS. 20A-G and FIGS. 21A-D. The graphs for FIGS. 20A-G are represented as % Survival vs. Exposure time (seconds (s)), while those of FIGS. 21A-D are represented as Log10 Count (colony) vs. Time (seconds (s)). As clearly shown in all tests, 100% of bacteria were killed within a short time frame of between 10 seconds and 50 seconds. As shown in FIG. 20A, a percent survival rate of 0% (100% death rate) for *E. coli* was observed after exposure to UV for 10 seconds. Similar 0% survival rates following exposure to UV light were observed for *E. hirae* (FIG. 20B—between 30-40 seconds), *S. aureus* (FIGS. 20C, 20D and 20G—20 seconds), *S. mutans* (FIG. 20E—20 seconds), and *P. aeroginosa* (FIG. 20F—20 seconds).

Figure 21A:
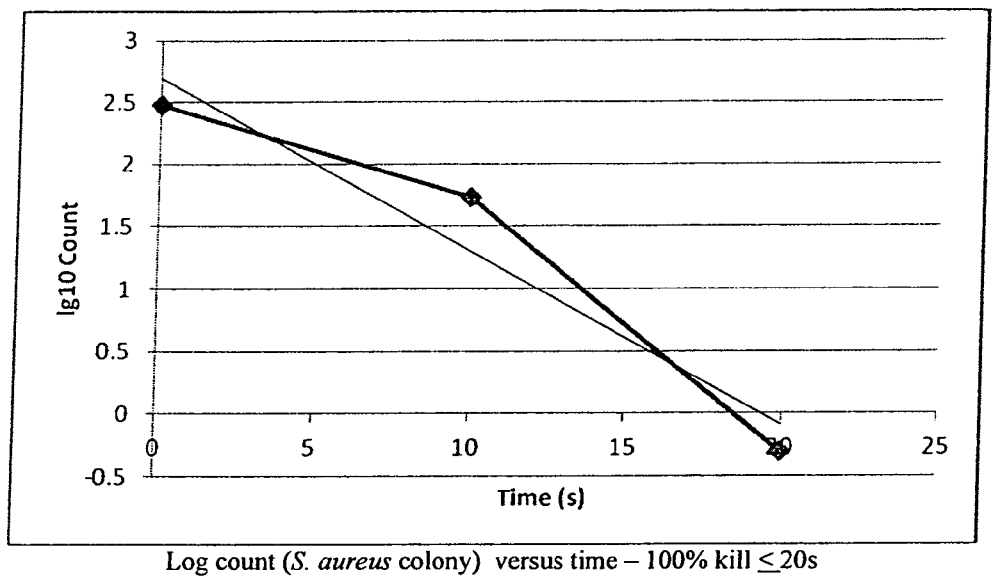
FIG. 21A to 21D are graphs of Log10 Count (colony) vs. Time (seconds (s)), illustrating the time required to achieve a zero count of bacterial colonies following exposure of rinse water to UV radiation energy prior to plating on agar plates.
Figure 21B:
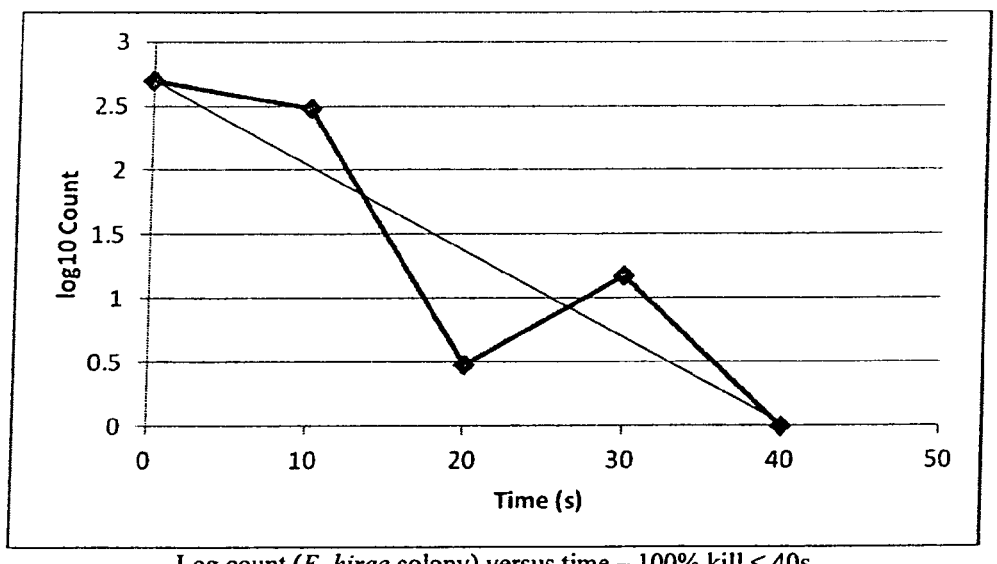
Figure 21C:
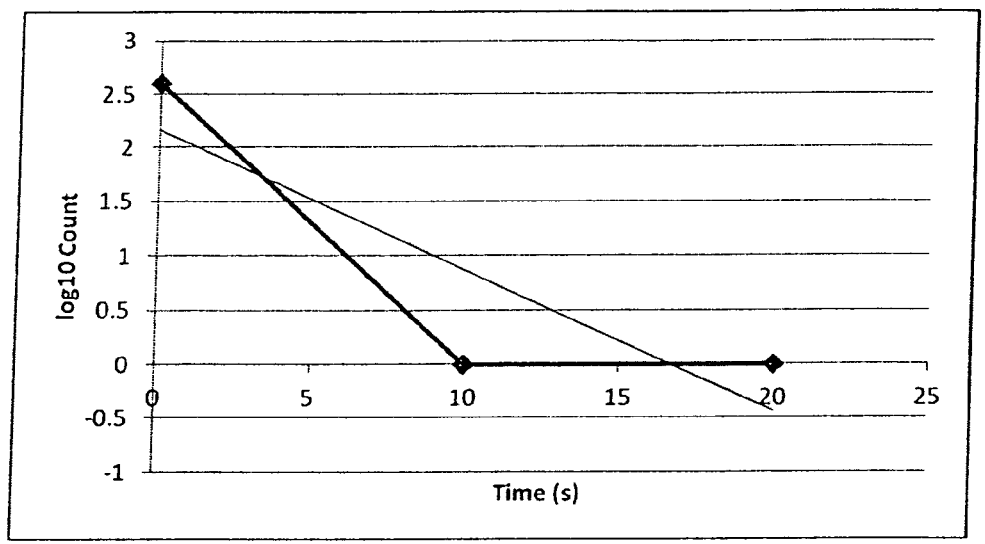
Figure 21D:
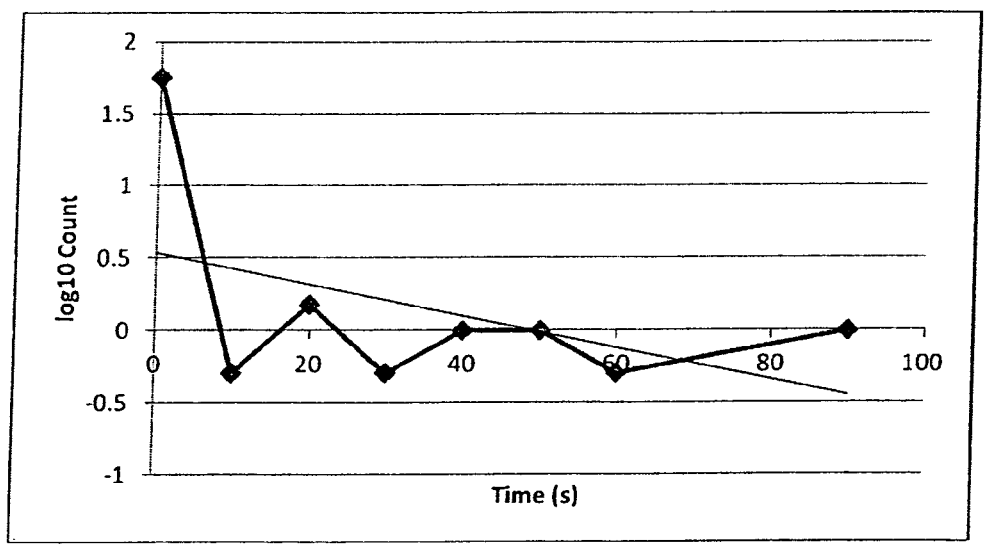

The above observation was further supported by plotting Log10 Count (Colony) versus Time (seconds (s)) to determine at what time a 100% kill rate was observed. For example, it was observed that zero colonies, that is a 100% kill rate, was observed after UV exposure for between 15 to 20 seconds (FIG. 21A—*S. aureus*), approximately 40 seconds for *E. hirae* (FIG. 21B), and less than 17 seconds but greater than 10 seconds for *E. coli* (FIG. 21C). For the milk residue colony tests, no colonies were observed on agar plates which were plated with it was found that no colonies (0% survival rate) were grown after exposure of the bottle containing rinse water to UV light for 50 seconds (FIG. 21D). As can be seen from the above results, it would appear that a sterilisation cycle of between 10 seconds and 50 seconds would be more than sufficient to attain a 100% kill rate for bacteria.

As demonstrated in the examples above, the hand-held and portable apparatus of the present invention, which does not require water, chemicals, or a microwave source, provides a convenient, efficient, and safe device for sterilising containers such as baby feeding bottles. The apparatus 1 of the present invention must be securely engaged with the flexible tab 10 so as to contact the micro switch 11 before the apparatus 1 is activated. Once the sterilisation cycle is completed, the bulb 6 and bulb 54 are automatically switched off. The material composition of the currently available baby feeding bottles is such that UV light cannot penetrate the polycarbonate construction such that harm comes to the user from exposure to UV radiation, thereby conferring protection to the user from the bulb 6 and bulb 54 when activated. However, if the baby feeding bottle is manufactured from polyethylene which allows UV light to pass through the polyethylene structure, the use of the shroud 80 or cover 200 protects the user from harmful UV rays.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A sterilising apparatus for sterilising a feeding bottle assembly for a baby, the feeding bottle assembly comprising:
   a feeding bottle having a top end and a base end, the top end having an open neck and a teat for the feeding bottle;
   the sterilising apparatus comprising
   a housing which is adapted to fit to the top end of the bottle and
   an ultraviolet (UV) light source on the housing which extends into the bottle for UV sterilisation of the bottle when the housing is attached to the bottle; and,
   an enclosed chamber into which the teat may be placed for UV sterilization.

2. A sterilising apparatus according to claim 1, wherein the housing is adapted to attach to and sit on the top end of the bottle, and further comprising a switch which automatically switches on the UV light source when the sterilising apparatus is attached to the bottle.

3. A sterilising apparatus according to claim 1, wherein the chamber further comprises a UV light source for UV sterilisation of the teat.

4. A sterilising apparatus according to claim 1, wherein the chamber is provided with a reflective surface for reflecting UV light.

5. A sterilising apparatus according to claim 1, wherein the feeding bottle assembly further comprises a teat-retaining ring for sealing engaging a teat to the open neck of the bottle fitted to the bottle and wherein the housing optionally attaches to the teat-retaining ring.

6. A sterilising apparatus according to claim 1, wherein the sterilising apparatus is arranged to be self-righting.

7. A sterilising apparatus according to claim 1, further comprising an electronic control that automatically switches off the UV light source when a sterilising cycle has been completed.

8. A sterilising apparatus according to claim 1, wherein the UV light source is deactivated upon detaching the housing from the bottle assembly.

9. A sterilising apparatus according to claim 1, further comprising engaging means which automatically engage the housing on the bottle assembly when the sterilising apparatus is fitted to the bottle assembly.

10. A sterilising apparatus according to claim 1, further comprising a shroud, the shroud being extendable for shrouding the bottle.

11. A sterilising apparatus according to claim 1, wherein the steriliser comprises a resiliently flexible tab which flexes upon attachment of the steriliser to the bottle assembly to activate the IJV light source.

12. A sterilising apparatus according to claim 11, wherein the flexible tab engages a micro switch connected to activate the UV light source.

13. A sterilising apparatus according to claim 1, wherein the UV light source comprises a mercury vapour bulb or a xenon vapour bulb.

14. A sterilising apparatus according to claim 1, wherein the sterilising apparatus further comprises a detachable cover for the housing, and wherein the detachable cover is dimensioned to accommodate a bottle.

15. A sterilising apparatus according to claim 14, wherein the detachable cover is adapted to block any UV light which passes through the bottle.

16. A sterilising apparatus according to claim 14, wherein the detachable cover includes a least one retaining member for retaining the bottle in position for sterilisation thereof.

17. A sterilising apparatus according to claim 16, wherein the retaining member is in the form of a seat for the bottle.

18. A sterilising apparatus according to claim 14, further comprising a safety mechanism to prevent emission of UV light for sterilising the bottle if the cover is not attached.

19. A sterilising apparatus according to claim 10, wherein the shroud is telescopically extendable, or is collapsible by folding upon itself.

20. A sterilising apparatus according to claim 1, wherein the housing comprises at least one closed chamber which separates any electronic control or power source from a remaining portion of the housing.

* * * * *

UNITED STATES PATENT AND TRADEMARK OFFICE
CERTIFICATE OF CORRECTION

PATENT NO. : 8,633,454 B2  
APPLICATION NO. : 13/321969  
DATED : January 21, 2014  
INVENTOR(S) : Anne Marie Durkin Page 1 of 1

It is certified that error appears in the above-identified patent and that said Letters Patent is hereby corrected as shown below:

In the Claims

Column 20, Line 18, Claim 11, delete "IJV" and insert -- UV --

Signed and Sealed this
Twenty-seventh Day of May, 2014

Michelle K. Lee
*Deputy Director of the United States Patent and Trademark Office*